(12) United States Patent
Froloff

(10) Patent No.: US 7,720,784 B1
(45) Date of Patent: May 18, 2010

(54) EMOTIVE INTELLIGENCE APPLIED IN ELECTRONIC DEVICES AND INTERNET USING EMOTION DISPLACEMENT QUANTIFICATION IN PAIN AND PLEASURE SPACE

(76) Inventor: Walt Froloff, 273D Searidge Rd., Aptos, CA (US) 95003

( * ) Notice: Subject to any disclaimer, the term of this patent is extended or adjusted under 35 U.S.C. 154(b) by 1011 days.

(21) Appl. No.: 11/215,910

(22) Filed: Aug. 30, 2005

(51) Int. Cl.
G06N 5/02 (2006.01)
A61B 5/00 (2006.01)

(52) U.S. Cl. .......................... 706/47; 600/300

(58) Field of Classification Search ................ 706/47
See application file for complete search history.

(56) References Cited

U.S. PATENT DOCUMENTS 5,676,138 A * 10/1997 Zawilinski ............ 600/301
2003/0187733 A1* 10/2003 Hertling et al. ............ 705/14

OTHER PUBLICATIONS

El-Nasr, M. Yen, J, and Ioerger, T. "Flame—Fuzzy Logic Adaptive Model of Emotions", Autonomous Agents and Multi-Agent Systems, 3, 219-257, 2000.*

* cited by examiner

Primary Examiner—David R Vincent
Assistant Examiner—Li-Wu Chang
(74) Attorney, Agent, or Firm—Walt Froloff

(57) ABSTRACT

A system and method of obtaining and processing emotive intelligence in electronic applications and devices is disclosed. This includes capturing author feelings. Feelings are assigned a pain-pleasure attribute and performance of string operations on the feelings attached text in performance of a service couple author intended meaning, satisfaction or motivation to degree of pleasure or pain associated with string text or string operations. The capability to capture and process emotive content allows for locating goods or services on a network, where providers anticipate a transaction on customer needs emotionally based.

Artificial emotive intelligence is applied in machine characters by endowing them with software entities of emotive states and associated intensities, and threshold values that trigger actions, with events triggering actions or behavior by threading through the character emotive makeup.

4 Claims, 12 Drawing Sheets

Emotive State Pleasure/Pain Table

| Dec (401) | Hex Code (403) | State Name (405) | Label (ES) (407) | Char (409) | Pleasure/Pain (411) |
|---|---|---|---|---|---|
| 0- | 0001 x000 | Aggressive | 1 | | Pain |
| 1- | 0001 x001 | Agonized | 2 | | Pain |
| 2- | 0001 x002 | Alienated | 3 | | Pain |
| 3- | 0001 x003 | Angry | 4 | | Pain |
| 4- | 0001 x004 | Annoyed | 5 | | Pain |
| 5- | 0001 x005 | Anxious | 6 | | Pain |
| 6- | 0001 x006 | Apathetic | 7 | | Pleasure |
| 7- | 0001 x007 | Apologetic | 8 | | Pain |
| 8- | 0001 x008 | Aroused | 9 | | Pleasure |
| 9- | 0001 x009 | Arrogant | 10 | | Pain |
| 10- | 0001 x00A | Bashful | 11 | | Pain |
| 11- | 0001 x00B | Blissful | 12 | | Pleasure |
| 12- | 0001 x00C | Bored | 13 | | Pain |
| 13- | 0001 x00D | Bossy | 14 | | Pain |
| 14- | 0001 x00E | Cautious | 15 | | Pain |
| 15- | 0001 x00F | Concentrating | 16 | | Pain |
| 16- | 0001 x010 | Confident | 17 | | Pleasure |
| 17- | 0001 x011 | Confused | 18 | | Pain |
| 18- | 0001 x012 | Curious | 19 | | Pain |
| 19- | 0001 x013 | Demure | 20 | | Pleasure |

FIG 4A – Emo State Graphic Set Table

| | | | | | | |
|---|---|---|---|---|---|---|
| 20- | 0001 | x014 | Depressed | 21 |  | Pain |
| 21- | 0001 | x015 | Determined | 22 |  | Pain |
| 22- | 0001 | x016 | Disappointed | 23 |  | Pain |
| 23- | 0001 | x017 | Disapproving | 24 |  | Pain |
| 24- | 0001 | x018 | Disbelieving | 25 |  | Pain |
| 25- | 0001 | x019 | Discouraged | 26 |  | Pain |
| 26- | 0001 | x01A | Disgusted | 27 |  | Pain |
| 27- | 0001 | x01B | Distasteful | 28 |  | Pain |
| 28- | 0001 | x01C | Ecstatic | 29 |  | Pleasure |
| 29- | 0001 | x01D | Embarrassed | 30 |  | Pain |
| 30- | 0001 | x01E | Enraged | 31 |  | Pain |
| 31- | 0001 | x01F | Enthusiastic | 32 |  | Pleasure |
| 32- | 0001 | x020 | Envious | 33 |  | Pain |
| 33- | 0001 | x021 | Exasperated | 34 |  | Pain |
| 34- | 0001 | x022 | Excited | 35 |  | Pleasure |
| 35- | 0001 | x023 | Exhausted | 36 |  | Pain |
| 36- | 0001 | x024 | Fearful | 37 |  | Pain |
| 37- | 0001 | x025 | Frightened | 38 |  | Pain |
| 38- | 0001 | x026 | Frustrated | 39 |  | Pain |
| 39- | 0001 | x027 | Grieving | 40 |  | Pain |
| 40- | 0001 | x028 | Guilty | 41 |  | Pain |
| 41- | 0001 | x029 | Happy | 42 |  | Pleasure |

FIG 4B – Emo State Graphic Set Table

| 42- | 0001 x02A | Helpless | 43 |  | Pain |
| 43- | 0001 x02B | Hopeful | 44 |  | Pleasure |
| 44- | 0001 x02C | Horrified | 45 |  | Pain |
| 45- | 0001 x02D | Hostile | 46 |  | Pain |
| 46- | 0001 x02E | Humiliated | 47 |  | Pain |
| 47- | 0001 x02F | Hurt | 48 |  | Pain |
| 48- | 0001 x030 | Hysterical | 49 |  | Pain |
| 49- | 0001 x031 | Idiotic | 50 |  | Pain |
| 50- | 0001 x032 | Indifferent | 51 |  | Pain |
| 51- | 0001 x033 | Innocent | 52 |  | Pleasure |
| 52- | 0001 x034 | Interested | 53 |  | Pleasure |
| 53- | 0001 x035 | Jealous | 54 |  | Pain |
| 54- | 0001 x036 | Leery | 55 |  | Pain |
| 55- | 0001 x037 | Lonely | 56 |  | Pain |
| 56- | 0001 x038 | Loved | 57 |  | Pleasure |
| 57- | 0001 x039 | Love struck | 58 |  | Pleasure |
| 58- | 0001 x03A | Meditative | 59 |  | Pleasure |
| 59- | 0001 x03B | Mischievous | 60 |  | Pain |
| 60- | 0001 x03C | Miserable | 61 |  | Pain |
| 61- | 0001 X03D | Negative | 62 |  | Pain |
| 62- | 0001 X03E | Obstinate | 63 |  | Pain |
| 63- | 0001 X03F | Optimistic | 64 |  | Pleasure |

FIG 4C – Emo State Graphic Set Table

| | | | | | |
|---|---|---|---|---|---|
| 64- | 0001 | x040 | Pained | 65 | Pain |
| 65- | 0001 | x041 | Paranoid | 66 | Pain |
| 66- | 0001 | x042 | Peaceful | 67 | Pleasure |
| 67- | 0001 | x043 | Perplexed | 68 | Pain |
| 68- | 0001 | x044 | Proud | 69 | Pleasure |
| 69- | 0001 | x045 | Prudish | 70 | Pleasure |
| 70- | 0001 | x046 | Puzzled | 71 | Pain |
| 71- | 0001 | x047 | Regretful | 72 | Pain |
| 72- | 0001 | x048 | Relieved | 73 | Pleasure |
| 73- | 0001 | x049 | Sad | 74 | Pain |
| 74- | 0001 | x04A | Satisfied | 75 | Pleasure |
| 75- | 0001 | x04B | Shocked | 76 | Pain |
| 76- | 0001 | x04C | Shy | 77 | Pain |
| 77- | 0001 | X04D | Smug | 78 | Pleasure |
| 78- | 0001 | X04E | Sorry | 79 | Pain |
| 79- | 0001 | X04F | Stubborn | 80 | Pain |
| 80- | 0001 | x050 | Sure | 81 | Pleasure |
| 81- | 0001 | x051 | Surly | 82 | Pleasure |
| 82- | 0001 | x052 | Surprised | 83 | Pleasure |
| 83- | 0001 | x053 | Suspicious | 84 | Pain |
| 84- | 0001 | x054 | Sympathetic | 85 | Pleasure |
| 85- | 0001 | x055 | Thoughtful | 86 | Pleasure |
| 86- | 0001 | x056 | Undecided | 87 | Pain |
| 87- | 0001 | x057 | Withdrawn | 88 | Pain |

FIG 4D – Emo State Graphic Set Table

EMOTIVE INTELLIGENCE APPLIED IN ELECTRONIC DEVICES AND INTERNET USING EMOTION DISPLACEMENT QUANTIFICATION IN PAIN AND PLEASURE SPACE

RELATED APPLICATIONS

This application references a previous filed application in a related field of invention; Ser. No. 09/563,624 filed May 2, 2000, entitled "System and Method for the Embedment of Emotive Content Into Modern Text Processing, Publishing and Communication"; patent application Ser. No. 10/445,758 filed May 27, 2003, entitled "System and Method For Creating Custom Specific Text and Emotive Content Response Templates For Textual Communications" and patent application Ser. No. 10/648,433 filed Aug. 25, 2003, entitled "SYSTEM AND METHOD FOR ENCODING DECODING PARSING AND TRANSLATING EMOTIVE CONTENT IN ELECTRONIC COMMUNICATION"

BACKGROUND OF THE INVENTION

1. Field of the Invention

The present invention relates to the field of emotive intelligence in electronic applications. More particularly, the present invention relates to accepting and processing emotive intelligence in Internet and E-commerce applications.

2. Background

Emotions and computers have, almost from the inception of these devices, been diametrically opposed concepts. Where computers calculate, humans reason. Reasoning has the emotive component that has heretofore evaded computer models and theories. Feelings are separate and different from thinking and vice versa. The intellect has little tolerance for the irrational. Emotions are accepted as a human shortfall in intellectual character. Even in areas such as law, the legal mind is taught to avoid inflaming the passions of the jury. The scientific teaching is to use cold logic in deducing, deriving and proving valid conclusions. In science, there is little allowance for emotion, as emotions tend to be unique in situation and circumstance, rarely predictable, repeatable or controllable. For these and other reasons, computer programs, communication and software applications have tended to ignore emotions, not the least of which is that they are fleeting and difficult to capture with any fidelity in an electronic format.

WYSIWYG display point & click keyboard interfaces are the current interface for helping us to tell our computer devices and receivers what we want. Not being Keats or Longfellows, most of us are not proficient in expressing feelings in written form, which are nevertheless naturally occurring with verbal communication in face-to-face interactions. Face-to-face communications by way of facial expressions, tone, body language and gestures form over 90% of our communications by some estimates. By and large, our modern interfaces allow only the text into email, web publishing, ecommerce, word processing, PDA/Cell, instant messaging, etc, electronic communications routinely filter out those amazing gestures, facial expressions, inflections and so much more which enable humans to make valid inferences about the true meaning and intent of the words conveyed.

Some studies suggest that of a communication received from a presentation, only 7 percent comprises the verbal or text portion. Therefore, much of the remaining 93% is emotive and non-verbal and is currently systematically filtered out through the device interfaces, mostly by point & click or typed text input. Because emotions are fleeting, spontaneous, unique to each individual, and ethereal to capture, technology in this area has not had much progress with the man-machine interface (MMI). Furthermore, emotions have been historically intellectually and culturally, technology's antithesis. Consequently, what is on a user's "mind" rarely makes it through the current electronic interface of most devices.

Electronic communication, at even the lowest levels, have "check sums" built in but these techniques have not been applied at the highest level of the communication. Thus a distorted or inferior signal yields ambiguous meanings, non-intended messages and erosion of relationships that increasingly depend on electronic communication via electronic applications.

MMI has in the past and is presently being studied and labs are busy trying to capture emotions through an interface because the potential benefits from capturing and exploiting emotive input is so great. The present methods are too imprecise to be of much value, but nevertheless used by determined users with emocons and emoticons. Finally, AI has been promising us more intelligent computers but with the exception of some Sci-Fi movies, has not addressed the emotional component of human intelligence for a multitude of reasons, which has led to AI's big failure. What are needed are interfaces that enable users to submit their feelings along with their textual messages, as they would ordinarily do in communicating with somebody standing nearby or face-to-face.

Textual communication, by its very nature can be ambiguous or obscure because of the multiple meanings in language. Emotive content from gestures, facial expressions, body language, and such have been used in conjunction with words to transmit meaning in language. Emotions are mostly absent with modern communication relying on text to carry the message. However, emotive content is used to focus the text and words onto the intended meaning out of a number of possible alternative inferences. Methods for embedding emotive content by a sender have been developed; see US Patent Application '624 from above Reference Section. These methods can be used to add emotive content by both graphical and textual mean. When emotive content is purely textual, understanding is further complicated for reasons such as imprecision in emotive intensity or ambiguity for lack of a more complete description of the emotive state. If emotive content is presented graphically, complexity is increased because the receiver is subjected to overtly emotional component much harder to ignore and impossible to decipher. Here, the receiver must "search themselves for an answer" or understanding. As it is now, the receiver cannot take advantage of computers to generate complete messages. Messages which ordinary human behavior and psychological principles are used to unravel the intended meaning in responding to received verbal messages. Hence, an entire band of communication lies dormant and unused in textual communication, oftentimes leaving little understood and counter-acting communications. What are needed are models and methods of processing emotive intelligence in electronic applications that enable the emotional intelligence dimension.

Emotive Intelligence

By reading an individual's heart or understanding their intent, motivation, action threshold and adapting programming to fit the individual's specific need, Internet models and software applications can use Emotive Intelligence (EI). EI is the underlying gut feeling, present intent, meaning, impetus, and motivation that automatically and uncontrollably occur in individuals without their conscious direction.

Individuals use Emotive Intelligence (EI) to make most decisions and initiate most actions. All feeling, intent, meaning, impetus, and motivation are contained in the El. Therefore an understanding and knowledge of an individual's mental state will disambiguate and clarify wants or needs, if intense to sufficient thresholds will prompt actions. Since many of these are well known, these actions can be anticipated from knowing the individual's mental state.

Psychologists have labeled the emotional decision making, X-brain, for the experiential brain, as distinguished from the R-brain, the rational part. The R-brain is the serial thinking brain that we use to process certain information and ideas through conscious effort. The X-brain is a parallel processor, which takes information from physical sensors, biochemical reactions, biochemistry, historical data stored in emotion memories, etc, and processes without conscious effort automatically producing a feeling resulting from the myriad of sensations that are received. We use emotional intelligence in every day face-to-face interactions. However, current computer device interfaces block all non-verbal communication, allowing mostly textual communication. Therefore currently, electronic processing, programming and communication streams only accommodate rational thinking R-brain functions. Support for the X-brain functions and hence intelligence is non-existent. What are needed are X-brain support functions for electronic processing and communications.

Internet services and product providers are added daily. To effectively find customers, vendors must know an individual customers "heart" or their specific feeling regarding the service needed or required to fulfill desires. Current attempts to capture emotive content use physical sensors, probes, blood pressure, sweat production, breathing, voice recognition and processing, prosodic, video processing/analysis, and other devices and methods. Usable models have not emerged and the Affective programming area is still in its infancy. A customers feeling or even what constitutes a feeling, is the mystery element which would allow programming to accommodate the individual, instead of probabilistic and statistical methods that attempt to use past user actions and demographics in lieu of specific individual needs and desires. For this reason, current methods are generally not determinative in ascertaining the individual's intent, needs, or motivations.

Alternatively, another knowing an individuals mental state can free the individual to have others make unsolicited offers to fill needs wants and desires, even anticipating an individual's actions to fill these him or her self. We currently do this daily when we complain or express feelings, knowing that this will elicit an offer of service from a friend, that service or act to alleviate the pain of the complaint or share in the pleasure of the expressed feeling. What is needed are electronic applications that can extend the area anticipated satisfaction of feelings to the Internet, which provides a universe of services and products looking to fill needs wants and desires.

State of the art attempts to infer, calculate or decipher an individual's mental state on a particular subject by sensors or other external devices has not been effective in bridging the gulf between individuals and vendors. Statistical methods have been tried but fall short. However, enabling the user to enter their own known mental state, with the knowledge that service will be much enhanced and actions anticipated from needs inherent in the Emotive Intelligence (El) provided, may prompt the user to take advantage by registering their mental state in connection with a particular subject or just their general mental state. The alternative is the present state of the art, having individuals consciously determining what they want and then attempting to find the service to satisfy the need, all through point and click interfaces.

The challenge is problematic, because emotions and mental states are complex, and nearly impossible to predict. However, individuals can introspect to discover his or her own feelings regarding prompted subject matter or feelings regarding themselves. Moreover, just like a well known friend observing an individual, applications applying an individuals feelings for inputs, can anticipate needs and enable sponsors, websites, providers and vender products and services to be customized to specific individuals by simply eliciting for the mental state or accepting a given mental states. Since El does not require label identification, anonymity can be preserved without affecting transactions. Thus what are needed are methods of accepting mental states into an application, and processing those inputs using emotional intelligent models and techniques.

Emotional Changes

Few things are as captivating, interesting or intriguing, as individuals emotional or status change. Although highly studied and taught in the artistic fields, this area has largely been ignored in electronic applications, other than to record and playback what actors performed. Moreover, this area of emotional intelligence is fraught with untapped resources and few methods or tools are available for electronic devices to process this information. What is needed are ways to import emotive conditions through electronic interfaces and use the emotive intelligence inherent in and similar to our own human processing, in enhancing electronic applications. The field of Artificial Intelligence has largely ignored emotive intelligence and so has failed to bring us computers and computer applications, which can use common sense or reason. Emotive intelligence is a vital component of common sense and reasoning, going beyond what binary or multi-valued logic can provide. What are needed are methods that provide the tools, structures and algorithms that enable the use of combining emotive illogic and cognitive logic.

Emotive Response

Emotive content carries the invisible dimension in intelligence, artificial and otherwise. There are many philosophies and ways of understanding and misunderstanding emotive intelligence. This makes computer models and applications that much more difficult to develop into a cohesive and consistent implementable programming models. Some of the challenge is currently handled statistically or with sophisticated demographics based methods, accessing disparate sources and obtaining facts collected in large databases, to derive and attempt to predict customer needs for positive responses.

An emerging branch of computer science called Affective programming attempts to apply emotive intelligence in electronic applications. However, Affective programs and models are at their infancy stages and struggle with cultural and technological deficiencies. What are needed are consistent and cohesive models that can be converted into software and used in electronic applications to increase their intelligence, ease of processing key parameters, and reduce the need for statistical guessing. What are needed are methods of anticipating buy-sell transactions that are more direct, have less guessing and more direct cause-effect relationships.

A problem encountered in some emotive intelligence models is the diversity of teachings on the subject, such that a clean all encompassing model is unavailable. Some teach that there are good and bad emotions, positive or negative. Some teach that there is a Devine Law that governs emotions and that they must be controlled. Some teach that we have no business manipulating others through their mental states; some that emotions are personal and private and should never see the light of a transistor. What are needed are clear models, not clouded with value judgments, not based on negative or positive emotions, not subjective, misapplied rules and concepts. What are needed are ways and methods to harness emotive intelligence as we generally apply this in ever day physical interactions. By adding this intelligence to applications, the applications range is extended and functionality increased to provide the untapped resource of human energy and driving force electronically emulating many of our actions and behavior carrying emotive intelligence. What are needed are ways to obtain, process and use emotive intelligence in games, email, ecommerce, PDAs/cells, Operating Systems and Interfaces, etc, to enhance and improve their functionality using El.

Requirements and Challenge of Future Interface

To be more effective and conducive to humans, the electronic device interface of the future must be richer in receiving user input and smarter at giving programming direction. One solution is to allow the interface to somehow read ones mind on command, or feel one's pulse as in a lie detector and some accompanying guess. People are ruled not only by cold logic but also by emotion. What are needed are systems and methods that enable access to users emotions, intent, motivation and hence to read the mind. The emotive content layer is a missing dimension in device interfaces and electronic communication in general. What is needed is technology that enables the emotive content layer without strapping electrodes and wires to users.

These are steep challenges but the payoff is enormous because once emotive objects are recognized and encapsulated by the interface, the system then has much more of the information regarding what a friend is saying, how well a search is going, a consumer's desires, wants, preferences, when they will make a decision, how/why a decision is reached, etc. What is needed is an interface that can grasp and encapsulate emotive properties, providing computer programmers the means to make non-linear interactive software programs and computer applications that are adaptive and customized to individuals. What is needed are tools that are non-linear, allowing the programming to make leaps and judgments not possible without many database demographics, probabilities and statistics or lengthy point & click streams. What are needed are adaptive algorithms able to change search strategies based on emotive content, progressively improving through subsequent emotive inputs. What is needed is an emotive content accommodating interface that can:

1) Enrich the interface input stream without over-burdening users,
2) Dynamically customize users input to users universe of content with request urgency and timeliness of response parameters,
3) Present the user with reasonable individual choices based on needs without prompting, as well as establish better defaults, automatic preferences, and options
4) Control the users environment to affect the comfort or resolution of the users needs without a lengthy dialog with a dumb interface,
5) Offer sponsors, vendors or providers of content better customer needs, wants, intent, motivation identification methods and distribution systems to satisfy those specific needs, wants, and desires
6) Ease the programming burden by working with robust emotive data objects instead of complex guess-work algorithms from tenuous models.

What is needed is:
1) Emotive input elicited from the user through emotive objects which capture the full set of emotions,
2) A standard format for the transmission of precise emotive content which can be embedded in text, audio and video application streams
3) Encapsulated emotive objects, data structures and transmission format allowing processing and a standard emotive content interface paradigm
4) Software engineering of an emotive content layer without resorting to by-guess inputs and by-gosh output options producing complex queries in prioritizing search results or eCommerce opportunities.

Artificial Emotive Intelligence (AEI)

Most current computer applications can benefit from the added dimension of El, the obvious ones are eCommerce, future OS, Web Publishing, E-mail and Instant Messaging, polling, polling and reporting continuously and without interpretation or analysis of polling results, PDAs-Cell phone and instant messaging interfaces, Set-Top Box interfaces, Applications requiring Measurable Emotive Feedback, Voting systems, Decision-making tools, Advertising, Complaint Desk, Games and appliance interfaces with personalities. Many more applications can use the missing dimension of El and one has only to name one before uses can be found for emotive intelligence.

E-Commerce Applications e-Customer attitudes, behaviors and preferences all stem from customer emotional makeup. People buy emotionally, not intellectually and those vendors that are astute and respond to hidden cues stand to gain a competitive advantage. Website owners operators and service or product providers are interested in on-line shopping behavior, brand loyalty, winning and keeping customers, anticipating customer needs because consumers can change vendors on a whim and they are very hard to win back. Vendors need to obtain basic emotional information on the consumer purchase decision cycle in real-time on-line. While present methods of doing this are expensive, time consuming and produce debatable results, what are needed are immediate measurable emotive satisfaction feedback which can be used adaptively on-line to customize the website for each individual user. Like mathematics, emotions are a universal language. Regardless of language, race, national origin or religion, most understand the emotive language basics. We grow to understand it early and quickly. Emotions are the big component of negotiations and business transactions. What is needed are ways to allow devices and electronic communication to provide the vehicle to better use these for satisfying customers and more quickly identifying unique customer needs to provider entities most likely to service those needs.

Web Publishing Applications

Publishing software makers require better more efficient and new ways of expressing or obtaining information through web interfaces. Emotive content provides a rich source of web publishing software structures and tools for eliciting emotive input from users and tools for using El in adaptively altering web content or better connecting with customized services.

E-mail and Instant Messaging Applications

Users of email currently, with some emails, have emoticons available, which they can insert into their transmissions. The old fashion method of words is available but prohibitively expensive on time and writing skill. The majority of us still put together an email message in too big a hurry to re-read for spelling, much less insert textual representative feelings to better describe the subject matter. Feelings, which ordinarily carry most of the EI information in fact-to-face contact, color the textual message with user intent and motivation. The emotional portion gives the message understanding, relationship, context and life. What is needed are tools to enable users to embed precise feelings quickly into text, as we all do currently in face to face contacts with facial expression, voice tone, and body language.

Index of Emotive Indicators

The Nobel Prize in economics in 2002 went to a psychologist, Dr. Daniel Kahneman, who helped pioneer the field of behavioral finance. Kahnemen persuasively argued that investors are irrational. But more than that, he showed that we are predictably irrational. Thus feelings are at the very foundation of our economic understanding, yet are under employed.

Turning to some economic conundrums, will foreigners continue to buy massive amounts of US government debt? Will short-term rates go to x.y % by this year? Can ten-year rates stay flat with a spread of only z % between the short-term rate and ten year bonds? Will the economy once again grow through the trend of 2-2.5%? Will the trade deficit grow or subside? Will the savings rate stay abysmal? Will the dollar drop or inflation rise? Will the government's deficits still top $300 billion? Will gold prices rise?

Are the central banks of the world going to keep plowing money into US bonds at an even bigger pace in 2005? Will long term rates stay flat? Will the yield curve flatten by this summer? Would the Fed continue to raise/lower rates, and risk an inverted yield curve? Would anyone buy a ten-year bond for a lousy extra 1% and then risk what goes with it? Is the US going into recession? Will long-term rates start to rise?

Historically, the Fed keeps on raising rates, with perhaps a pause or two, until it gets to at least 4%. Once the Feds get started, they do not stop until there is some pain. Since the signals of "economic pain" tend to lag, it is quite possible the Fed tightens too much before it stops. The reason for the lag is that most economic data is a few months old before anybody can get it, or even establish an actual trend.

That is not good for bonds, and it is not a good environment for credit spreads. When credit spreads are "tight" it indicates that the difference between a government bond and other bonds is historically very low. And by tight, the meaning is no room, or very little, to get any tighter. When interest rates are so low, investors look for any place to get higher yields. If they pour into high yield bonds, corporate bonds, and emerging market debt, the yield on those bonds relative to government debt has to come down, making it a fairly risky proposition for those playing the spread game. The Fed will continue to raise rates until the economy shows signs of trouble. While the Fed in the past has been willing to cause a recession, they are on the seesaw between worrying about inflation and creating another speculative economy with interest rates too low and the concern that raising rates too much will squeeze the growth out of an economy that has grown addicted to, if not dependant upon low interest rates. If long-term rates do not rise, the Fed will stop sooner than 4% because they will not create an inverted yield curve on their own.

These are all market forecast questions and issues, and people making decisions need to know what consumers, government officials, bankers, etc are feeling. After all, the market can be irrational longer than you or I can remain solvent.

Polling is the current state of the art in ascertaining people's expectations, confidence and feelings. A current polling solution is made for characteristic data figures of merit in economic activities and an index of those factors for indications of where the economy is going. However, this approach is based on circumstances and information that is reflective of economic activity, activity that is time consuming to extract, secondary and tertiary in causation, and not fundamental to feelings or even on the nations pulse. Moreover, lags in this knowledge cause immense problems because much is at stake and stale data is bad data. Counting all the ifs and buts is revealing on just how badly money managers and authorities need to know how confident, scarred, fearful, angry, interested, relieved, suspicions, withdrawn, optimistic, aggressive, cautious, anxious, etc certain populations are at anytime. What are needed are ways that this data can be acquired in real-time continuously by simply monitoring communication data streams for emotive content anonymously. Eliciting this for this data expressly can also provide sample data representative of any demographic. What are needed are software products to accomplish the extraction of leading emotive indexes from data in specific areas of economic or financial activity. These can be had by continuous real-time emotive-content monitoring of communication streams for the nation's "pulse" and other vital signs.

Voice-Mail Applications

Individuals are turning to applications of emotive content in phone applications. At least one such system, Emotive Alert, labels messages according to the caller's tone of voice to identify which messages are the most urgent. The software system might be installed at the phone exchange or in an intelligent answering machine, where it will listen to incoming messages and send the recipient a text message along with an emoticon indicating whether the message is urgent, happy, excited or formal. As machines and devices do more and more, emotional intelligence must be introduced so that software can serve us better. Currently, these external means to bring in emotive intelligence are limited, not cohesive, making them islands without bridges to connect these kinds of applications with other applications.

Machines and Appliances with Personalities

Home networks will eventually establish connectivity between humans and most major appliances in the home. If you believe the SciFi movies or futurologists, many of these devices will eventually have voice input/output interfaces. Rather than the Steven Hawking robotic voice, text streams with emotive content and prosodic interfaces can give machines personalities and a human quality currently only dreamed of by visionaries but currently a reality via emotive layer enhanced text streams bound for prosodic voice I/O interfaces. What is needed are emotive standards which can tie emotive inputs from voice recognition devices to EI processing methods and then to emotive output prosodic interface devices. Appliances with personalities and home networks that are attuned to the occupant's feelings, physical, emotional and cognitive can be fed streams of emotive embedded text streams. This frees up users to interact with and understand machines naturally, rather than constantly adjusting machines to stay comfortable, safe, and well maintained.

PDAs-Cell Phone, Instant Messaging Interfaces

These devices all have displays, which can use the emotive interface and transmission capability to enrich communication and provide smarter services. These can be exploited in verbalizing text or email messages with the appropriate emotive inflections for aural interpretation, making communication richer and more versatile.

Set-Top Box Interfaces

The TV of tomorrow is here today but with the same point and click interface of yesterday. What is needed is a box that can receive a simple emotive instruction, "Computer, I'm feeling very cold" and that command should command the home heating system to increase the temperature setting 5, 10, 15 degrees depending on the intensity of the feeling, without forcing the individual to log into the Interactive TV or set top box, click their way to the home-network, choose the furnace and dial in a new temperature setting. Physical sensation is not the only layer of feelings. Personal and social-induced feelings should be handled as well. Where the feelings are pain producing, actions to reduce the pain could be automatically taken or options offered for such. Where the feelings are pleasurable, these can be used to share with friends or even actions to maintain or increase the pleasure feelings can be offered as smart options. In either case, the Operating System (OS) becomes much more intelligent at anticipating a users point and click input, doing much of the non-creative but informative "thinking" by way of instant searches for options, and allowing the user to more quickly decide on action which would otherwise take him much longer or never reach that alternative.

Google currently provides a cell-phone service whereby the consumer dials a number on their cell/PDA and all the pizza establishments within a certain radius are identified and phone numbers provided. Application of emotive intelligence would anticipate such needs from the hunger feeling. In a scenario wherein one comes home and issues a command "Computer, I'm feeling extremely hungry", the home interface application may check a list of favorite meals which can be prepared within the time set for "extremely", 10-15 minutes, check the refrigerator and cupboards for available ingredients and let consumer know instantly what they have available and a list of restaurants within X radius which can be called beforehand by computer to ascertain wait time or to establish a reservation should that be necessary. This is all that a companion might do in knowing that you are "extremely hungry", thus this intelligence can also be programmed with the input of feelings.

Scenarios like the above abound. As the Internet grows in limitless ways and services are all out looking for ways to satisfy consumer needs, but currently mostly using passive advertising or random spam or spam-like methods. The myriad options available boggle the mind, hence methods are needed to narrow the list of options to find the most likely needed service in the quickest possible time, and fulfill a specific desire for a particular person within the desired time constraint.

Applications Requiring Measurable Emotive Feedback

Psychologists, social workers and therapists need to measure and report client progress. Funding is based on worker showing measurable results of therapy/progress. This is currently and very difficult to assess and record by current methods and requires periodic time-consuming "assessment" reports. Therapists listen and record clients "presenting problem" and elicit the associated emotive content on the presenting problem. This is the initial state. What is needed to simplify and structure the progress reporting is upon termination or periodically, the presenting problem emotive content is elicited and the emotive displacement or emotive change calculated. Measurable satisfaction or dissatisfaction is then linked to success or failure of therapeutic approach taken, incremental success is measured by increase in pleasurable emotive intensity or decrease in painful emotive intensity, and incremental ineffectiveness is measured likewise. Methods of eliciting and calculating the emotive metrics are needed.

Decision Facilitation Interfaces

Decision-making programs that account for the emotional element are also likely to be more reasonable than applications and methods using only logic, as logic is binary and one-dimensional in nature. For example decisions could be made not on the probability of an event happening, but on the decision makers emotive disposition regarding a particular subject matter. Since many decisions are made based on insufficient or imperfect information, emotions play a big part, going deep into the subconscious database for a past data point. Decisions made emotively and times "gut feel", apply a storehouse or database of experiences that is associated with feelings. Applications that elicit precise emotive content with issues, criteria and alternatives, are embedded with emotional content that can be used to derive the least painful, most pleasurable or most favorable solution, resolving many conflicts which must be weighted or just. Methods are needed to elicit, extract, combine and formulate results from the feelings space in decision-making processes, which most closely model human decision-making. This would enable machines and appliances to act more "reasonably" and to be more "human" without sacrificing their functionality and usefulness.

Voting Interfaces

Voter systems that allow emotive choices concerning issues and or candidates, are more likely to provide the true choices on issues than the current "forced" binary yes/no choice systems. For example, apathy is a neutral emotion, which is not often a factor because voters are not motivated to expend the effort to vote. Since emotions are the major underlying motive for voting and can be ascertained easily through emotive objects, mass profiling of emotive input can be used to resolve issues on the most fundamental of levels, the peoples feelings.

Encryption-Decryption Streams

Most streams currently need some sort of privacy assurance. Emotive objects provide additional elements/tokens from which ciphers can be based and which are perhaps easier to key on. Keys can be easier because emotive may be more deeply embedded in memory and more likely to be event based. Combinations of emotions as well as emotion profiles can be used for encryption-decryption of data streams.

Overcoming "Click Fraud" in Online Advertising

Thousands of merchants currently pay for click stream directed to their website, paying as much as $50 per click. Many of these are being victimized by "click fraud" which are bogus streams generated by fruitless traffic from scammers paid to generate clicks on a website with no intention of ever buying anything. Although search engine providers issue refunds for these types of fraud, fraudulent clicks frequently exceed spending limits and knock ads out of the display rotation. They also don't compensate merchants for missed sales opportunities.

Search engines such as Google's have implemented auction advertising links and many other business models are now emerging which allow search engines to be more and bigger market place advertisers. This advertising market is expected to grow to $7.4 billion by 2008, but is threatened by "click fraud".

In face-to-face sales, a seller searched the buyer's face to discover the emotions, motivations and attitude of the buyer, upon which he can trust in negotiations, price, risk of non-payment, etc. This is currently not possible in eCommerce and Internet transactions. Emotive objects provide a way to access user emotive content, and programmably use this information as a real live seller would do in understanding the buyers motivation and intent to purchase, and what the buyer is truly motivated to purchase.

Accessing users emotive content, would give websites a way to programmably filter those with serious intent and potential to purchase over those that are just clicking for mischief. Albeit, as in real life, there will be "actors" who will attempt to circumvent or gain advantage through emotional tactics but there are also those users who will just be genuinely interested in quicker unique service, customizable products/services and more reliable results. Making tests like the Solomon Test is doable with emotive objects as the emotive state and intensity are available parameters and decisions can be based or driven by any programming complexity desired.

Complaint Desk

Whether complaints come over a network or face-to-face contact, the emotions of the consumer will drive his/her need for a satisfactory solution. This is called "straightening feathers" and almost entirely depends on satisfying the emotional perturbation stressing a consumer of a product or service. At times the solution consists solely of a de-escalation of initial emotive intensity. At times the emotive state and intensity can drive the solution options, i.e., a highly emotionally intense individual is likely to require more time and attention than an individual with less of an intense reaction. Another, perhaps seeking a small token of compensation for the deficiency, rather than an individual with personal issues misdirecting an emotion would be handled differently. Therefore, knowledge of the magnitude and type of the emotional content will reveal the work required to achieve equilibrium or the solution that generally brings about a satisfactory result. Also knowing the emotive state, oft times very apparent in face-to-face contact, if not dealt with, serves only to exacerbate the painful feelings of consumer/client who may return in another less manageable form. The beginning of any solution will require the grievance stated and associated emotional content because a good solution will require that both be satisfied. What are needed are ways to calculate satisfaction from emotional circumstances.

Game Applications

Most games currently carry very few emotional states, hate or fear among the dominant. These motivate the players to kill, maim, injure or otherwise wreak havoc to score points either in offense or self-defense measures. Although wildly successful, the most common complaint is that they lack intelligence or options for different strategies beyond the obvious linear brut-force mentality. While providing excitement of a salable game, there are other markets, which are left out, the girls market for example, or users who would think like to think more strategically or users who want a more "satisfying" victory. Also, the games can become boring because of the lack of dimensionality, kill or be killed being the only goals. For example, the introduction of the emotional dimension into most games, would add complexity, intelligence and options to grow the game itself. Character auto response and character decision-making actions would provide additional options and strategic directions.

Hence the emotive intelligence component can become a strategic element which would make the game "deeper" than a straight shoot'emup, yet retain fun by virtue of giving the player the option of always going back to the brut-force play, the mindless killing and violence. Thus, what are needed are more "intelligent" games.

SUMMARY OF THE INVENTION

This invention discloses a system and method of obtaining and processing emotive intelligence in electronic applications and devices. The steps include receiving an author's emotive state from a set of emotive states, and an associated emotive intensity from a range of intensity. This capturing of the author's feelings is done via an application interface using graphical, textual or aural means, allowing the author to select the emotive state, associated intensity, and any associated input text.

A pain-pleasure attribute is assigned to the emotive state, attaching associated text with the captured feeling and the assigned pain-pleasure attribute. Performance of string operations on the attached text in processing the input, allows coupling of the author's intended meaning, satisfaction or motivation to degree of pleasure or pain associated with string text.

Actual calculations of raw emovectors includes mapping the emotive vector to an n-dimensional space with pain-pleasure and time dimensions wherein vector operations on the emovectors yield resultant pleasure-pain values or by defining a two-dimensional space wherein pleasure and pain axes are aligned in opposing directions orthogonal to a time axis and performing algebraic operations to obtain net pleasure-pain from emotive shifts in time. Since emotions are constantly changing as we experience events, so must the electronic domain accommodate and interpret these changes. More than one emovector from an author gives rise to the processing of emotive shifts. These emotive shifts or emotional changes maintain their association with the text, coloring the process with additional meaning and attributes that relate directly to the author.

In an embodiment of the inventions, the capability to capture and process emotive content allows for locating goods or services on a network based on emotive content, from providers anticipating a transaction based on customer needs emotionally based. Authors, aka users, consumers, clients, and senders send emotive content to providers of goods and services, the provider having emotive content preferences. Providers compare received emotive content with provider emotive content preferences, and make offers of goods or services to authors with emotive content corresponding to provider's customer emotive content profiles. Thus emotive intelligence narrows an author's search for providers desiring to satisfy a particular market customized needs, needs that include temporal and geographical constraints. Temporal constraints are inferred from the text and emotive intensity; geographic constraints are authors' location, providers' location and the effort/time it generally takes to provide the good/service required. Furthermore, before and after service emotive content shifts can be processed to alter further service in a customized fashion based on author satisfaction as calculated using a net pain-pleasure of given customer feelings. These feelings can travel in sequences and have priorities, and in an embodiment of the invention a model is given below to accommodate those challenges.

Artificial emotive intelligence can be applied to characters by endowing them with or representing them as software entities with emotive states and associated intensities, and threshold values that trigger actions. This set of emotive state entities would constitute the character emotive inventory, much like our own emotional makeup. Thus scenario events and circumstances trigger specific character emotive states/intensities from an emotive inventory, and these emotive signals exceed the set thresholds they trigger character actions. Character actions occur based on the reactions of emotive states, intensities, and thresholds reached, thus providing autonomy and intelligence to the character. A prosodic interface fed from a source of text and emotive content endows a machine character with perceived emotional intelligence.

BRIEF DESCRIPTION OF THE DRAWINGS

These and further aspects of the invention, may be better understood with reference to the accompanying specification and drawings depicting the preferred embodiment, in which:

FIGS. 4A-4D is a table of an emotive state set with emotive state names in alphabetical order and associated hex code order, graphic representation, label, and pain/pleasure attribute designation.

DESCRIPTION OF THE EMBODIMENT

Objectives

Objectives of the invention in no particular priority are as follows:

To establish Emotive Intelligence in devices and Internet

To enhance electronic applications with the Emotive Content

To provide methods and models to absorb emotions through electronic and device interfaces, and to provide cohesive models and methods to process emotive intelligence in electronic applications.

Cycle of Operation

A simple cycle or mode of operation over a computer network would involve a plurality of computing devices on a network with computing devices that can display graphical and textual output. Applications executing on devices would facilitate exchange of emotive vectors from author/sender emotive information by associating author emotive state from libraries of emotive states, with author/sender normalized emotive intensity from ranges of intensities, assembling emotive content by associating emotive vectors with associated text, encoding emotive content, preserving association of emotive vectors with associated text and transmitting the communication with emotive content to one or more receiver computing devices. Receiving computing device applications parse communication received, mapping emotive vectors to graphical representations from sets of graphical representations for display or to processing the emotions with the associated text stings that add emotive intelligence to the application. Emotive intent, motivation and meaning can be synthesized from the emotive and associated text, the interests which come about in the association of feelings, their degree and direction in satisfying an individual's interest as coupled with the associated text. These are the basics, which are applied to most electronic applications magnifying or enhancing their primary function with emotively intelligent features. An aspect of the invention is that all emotions and feelings are signals, which are good and positive, even such "down" or "negative" emotions such as anger and depression. A Feelings model associates the emotive states with attributes of pain or pleasure, to which the emotive intensity then represents the degree of pleasure or pain that is to be attributed to a particular emovector coupled to the associated text, conferring or attributing the subject matter or action with the emotive intent or motivation.

Hardware Context

Figure 1:
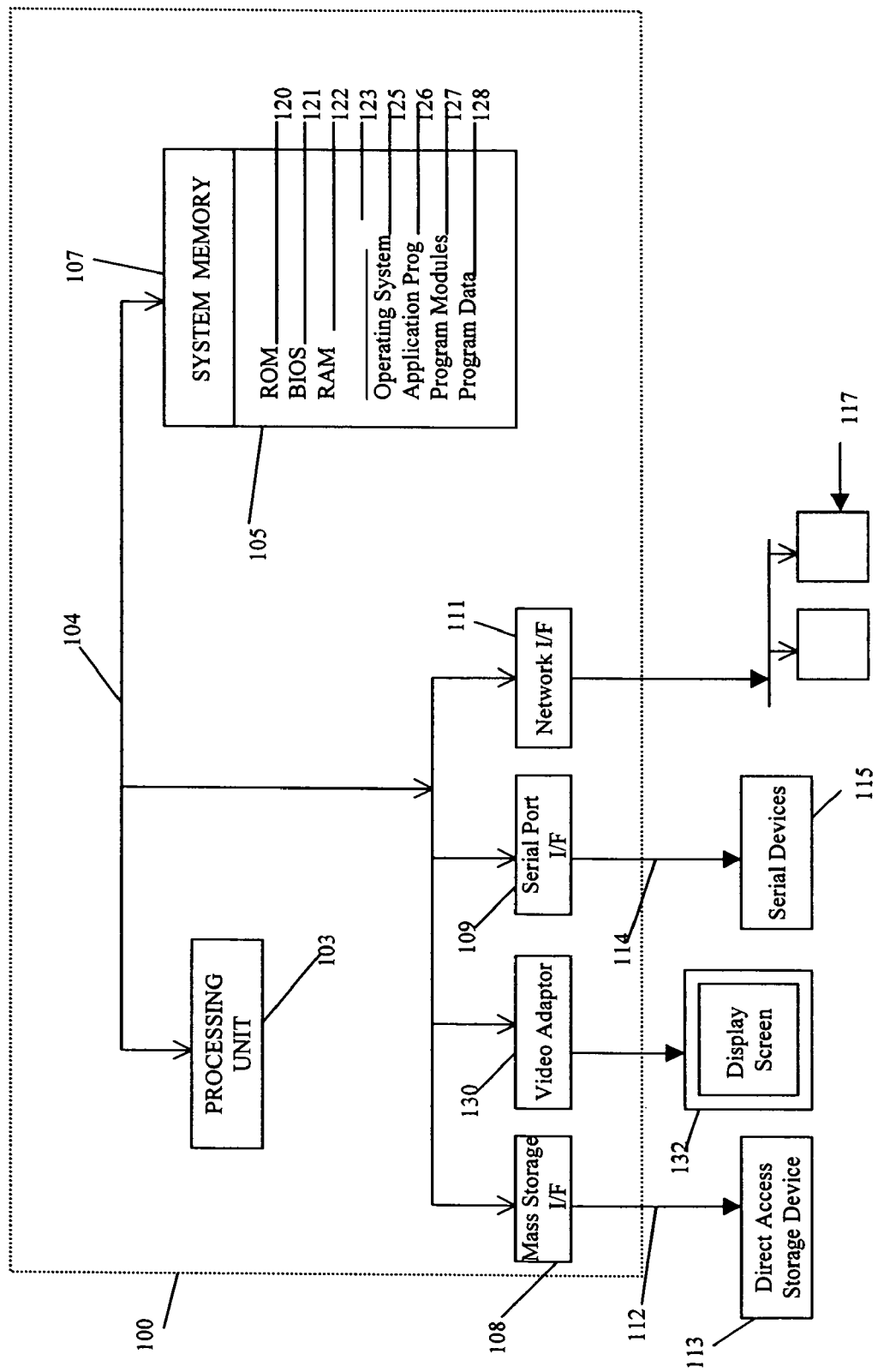
FIG. 1 is a block diagram illustrating a typical computer system for residing and executing software for aspects of the present invention.

FIG. 1 is a diagram showing a computer system 100, which can host applications enhanced with embodiments of the invention. In one embodiment, the computer system 100 is a typical networked computer, workstation or server with at least one Central Processing Unit 103, Memory 107, network interface card 111, Display Screen 132, Mass Storage interface 108 for such devices 113 as hard drive(s) removable disk drives, optical disk storage, floppy drives, I/O buses 112 and 114, Memory Buses 104, etc. For purposes of illustration, embodiments of the invention are provided in the context of a word processor, publisher, email, e-commerce, games, and device applications program.

Computer system 100 includes at least one processor unit 103, which obtains instructions and data via a system bus 104 from a main memory 107. Illustratively, the processor is a PowerPC available from IBM or a Pentium level processor from Intel/HP/SUN etc. More generally, however, any processor configured to implement the methods of the present invention may be used to advantage. The main memory 107 could be one or a combination of memory devices, including Random Access Memory 122, dynamic, nonvolatile or backup memory, (e.g., programmable or Flash memories, read-only memories, etc.) and the like. In addition, memory 107 may be considered to include memory physically located elsewhere in a computer system 100, for example, any storage capacity used as virtual memory or stored on a mass storage device 113 or on another computer coupled to the computer system 100 via system bus 104. Illustratively, the main memory 107 contains executable programs, which manage the hardware and control the software programs 105. The ROM 120, BIOS 121, and Operating System 125 are a system of programs, which manage the hardware and software resources for the use and running of application programs. The memory 107 further contains application programs 126 specifically, an email, word processor, text editor, publishing tool, web builder etc for purposes of an embodiment of the invention. In one embodiment, the application is an email application. Since email applications have been ported to almost all platforms and operating systems currently in use in the market place, these can all eventually benefit from aspects of the present invention and serve to broaden the scope of the invention. Program modules 127 and Program data 128 would typically also be resident in main memory 107 along with other programs 125 which can be paged or swapped in from other memory sources, local 108 or networked 117. Software components and objects are but parts of programs, which reside together in various regions of addressable memory and are executed to produce the necessary application functions. Software components and objects themselves can be broken down into data structures and programming logic which use the data structures. Generally, program modules 127 include processes, programs, objects, components, data structures, etc. that perform particular tasks or implement particular abstract data types.

The computer system 100 includes a number of operators and peripheral systems. Illustratively, these include a mass storage interface 108 in communication with storage device 113, which can be such devices as hard disk drives, optical disk drives, CD/DVD, portable memory, floppy disk drives, memory sticks/cards, optical storage, at least one input/output (I/O) interface 109 coupled to I/O devices 115 such as modems, wireless broadcaster devices, audio, communication via serial protocol bus 114 such as IEEE 802.xx, Firewire, USB, RS232 etc, and a network interface 111 coupled to a plurality of networked devices 117 which can be mass storage, other computers, wireless devices and other networked devices. The I/O devices 114 may include any combination of displays, keyboards, track point devices, mouse devices, speech recognition, prosodic devices and the like. In some embodiments, the I/O devices are integrated, such as in the case of a touch screen or display panel. The networked devices 117 could be displays, desktop or PC-based computers, workstations, or network terminals, wireless handheld or other networked computer systems. As such, aspects of the invention can be practiced on a single computer system as well as over a network of computer devices.

A number of program modules may be stored on the mass storage device 113, ROM 120 or RAM 122, including an operating system 125, one or more application programs 126, other program modules 127, and program data 128. A user may enter commands and information into the workstation 100 through input serial devices 115 such as a keyboard or pointing device. Other input devices (not shown) may include a microphone, joystick, game pad, satellite dish, scanner, or the like. These and other input devices are often connected to the processing unit 103 through a serial port interface 115 that is coupled to the system bus, but may be connected by other interfaces, such as a parallel port, game port or a universal serial bus (USB). A monitor 132 or other type of display device is also connected to the system bus 123 via an interface, such as a video adapter 108. In addition to the monitor, computers typically include other peripheral output devices (not shown), such as speakers and printers.

The computer workstation 100 may operate in a networked environment using logical connections to one or more remote computers, such as a remote computer 117. The remote computer 117 may be another computer, a server, a router, a network PC, a peer device or other common network node, cell-PDA and typically includes many or all of the elements described above relative to the computer 100. The logical connections depicted in FIG. 1 include a local area network (LAN) and a wide area network (WAN). Such networking environments are commonplace in offices, enterprise-wide computer networks, intranets and Internet.

When used in a LAN networking environment, the computer 100 is connected to the local network 117 through a network interface or adapter 111. When used in a WAN networking environment, the computer 100 can connect via modem 115 or other means for establishing communications over the wide area network 117, such as the Internet The modem 115, which may be internal or external, is connected to the system bus 114 via the serial port interface 109. In a networked environment, program modules depicted relative to the computer 100, or portions thereof, may be stored in the remote memory storage device. It will be appreciated that the network connections shown are exemplary and other means of establishing a communications link between the computers may be used. Computing devices with wireless communications such as cell phones, text message devices, GameBoys, PSPs, PDAs, cell/PDAs or other handheld devices running electronic applications in hardware may be used.

Emotive Alphabet—Encoded Glyph Tokens

Figure 2:
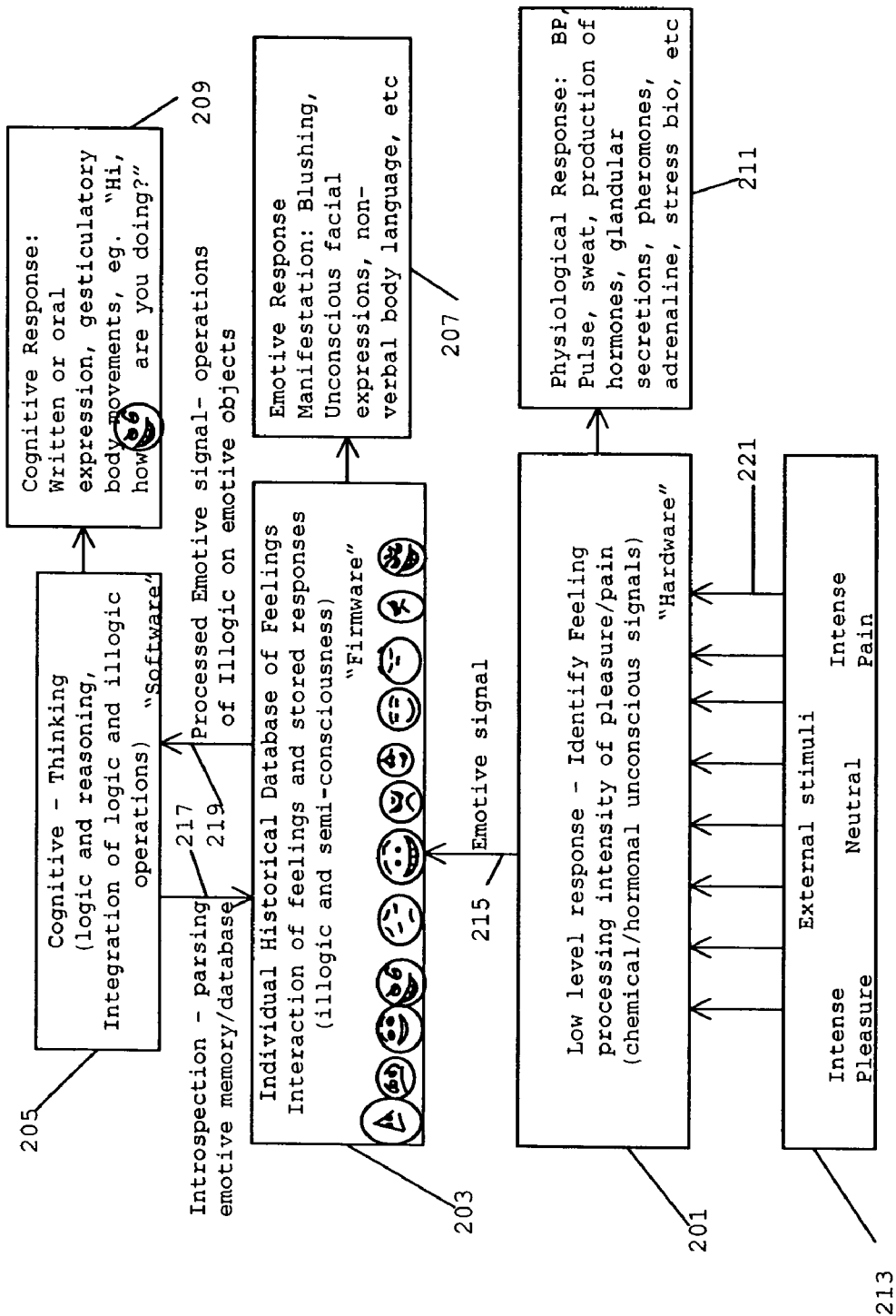
FIG. 2 is a block diagram of the basic human emotive response model in accordance with an embodiment of the present invention.

FIG. 2 is a block diagram of the basic human emotive response model in accordance with an embodiment of the invention. Referring now generally to the figures and particularly to FIG. 2, FIG. 2 is an illustration of an exemplar basic human response model.

External stimuli 213 can provide physical signals of degrees of pleasure, such as warmth and comfort, or pain, such as temperature extremes hunger physical discomfort, etc. These signals 221 of degrees of pain are inputs to the Low Level response 201 which manifests in physical or physiological responses 211 such as blood pressure (BP), sweat, hormones, glandular secretions, adrenaline, digestive juices, stress chemistry, proteins, enzymes, medications or pharmaceuticals, mood altering chemicals, etc. These low level responses to physical or internal biological reactants and stimulants generate emotive signals 215 which then trigger a resultant emotive response 203 or emotion from the individual's historical database of feelings and memories, which can promote themselves to the conscious cognitive level 205 of thinking and logical reasoning, via an emotive signal 219. An individual can also "look inside" or "check in" by introspection 217 to ascertain his/her feelings on a particular subject matter. A typical introspection can include a given range or scale bounded of intensity by the least and most intense feeling experienced by the introspector, so that the introspection can be framed and normalized to the author/sender of the feeling, ultimately answering the how intense is the feeling question in a bounded sense. The introspection can be very quick or occur over much time of contemplation, depending on the subject to be pondered and the complexity and intensity of the associated feelings. A cognitive response 209 will then comprise the textual/verbal couched in the emotive content, which forms the basis, intent, motivation and or meaning for the textual/verbal manifestation. An embodiment of the invention embeds, parses and processes the combined communication 209 for the full message, and therefore can generate emotively intelligent outputs. Thus the emotive content will include text or words that will be colored or affected in meaning. This cognitive output can then become input to a device or application. In order to cross the application or device input interface, a feeling will have a stated name and an associated intensity within a scaled range bounding the feeling. The emotive intensity can be given as a value or descriptive string or word qualifying the feeling.

Multiple Emotive States

We experience emotions in different ways as well as different times. Furthermore, we can experience several emotions simultaneously or in quick succession. At times, those emotions in quick succession are difficult to catch because of the complexity of the feelings experienced so closely together in time may mask one another. However, an aspect of the invention allows that one or more emotive states/intensities can be present in association with selected text. Moreover, the experienced emotions may or may not transpire concurrently with message generation. Thus through an aspect of the invention, feelings can be handled by principles of superposition, by taking each identified feeling separately and applying it to the common subject matter, the text generally, connected with other feelings. Furthermore, identifiable groups of emotions occurring together or in characteristic sequence can be a signature or establish a pattern for an emotional process, which although adds complexity, also adds information to better interpret the intended meaning or intended meaning of the associated text.

For example a person can be exhausted, grieving, and in physical pain over some event or occurrence. Those separate feelings may all have intensities that an individual with introspection can discern and discover. As with most other things, introspection becomes better with practice but most are able to attain the minimum level required. Introspection can reveal one or more feelings on a subject and each feeling would have a state and intensity. In an embodiment of the invention, the encoding scheme allows multiple emotive state/intensity pairs for the same text by attaching the multiple emotive tokens representing the emovectors a particular text string(s). Processing the emotive content can then decouple the datastream and using the principles of superposition of emotions, treat the emovectors as independent tokens, using the vector properties of each as though they were independently operating on the text and each other.

Feelings Priorities

Figure 3:
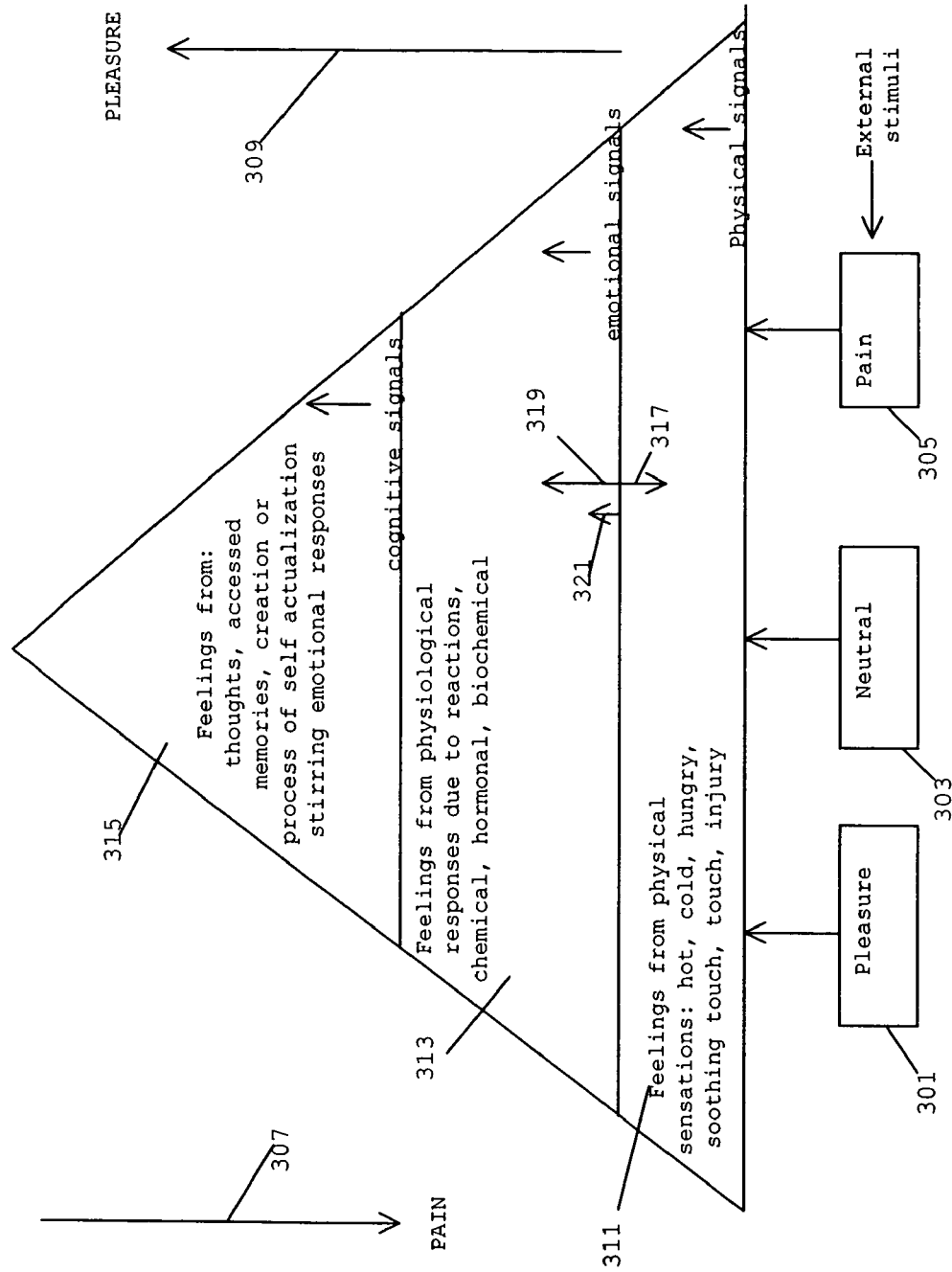
FIG. 3 is an illustration of an emotive hierarchy model in accordance with an embodiment of the present invention.

FIG. 3 is an illustration of the emotive hierarchy in accordance with an embodiment of the invention. The similarity between the FIG. 3 model and Maslow's Needs Hierarchy model is by analogy. Maslow's Hierarchy of Needs model loosely rests on the more fundamental emotive hierarchy model shown as an embodiment of the invention in FIG. 3. The feelings 311 evoked from physiological sensation from pleasurable 301 neutral 303 painful 305 external stimuli of temperature, hunger, touch, injury, etc. are generally more immediate and more intense, causing an individual to pay more attention to satisfy those feelings over other less dire immediacy feelings from internal stimuli, or "mood" altering biochemistry. Feelings generated from internal physiological 313 stimuli such as biochemical changes from adrenaline, hormones, testosterone, estrogen, pheromones, endocrine, arousal, etc are generally less automatically reflexive prone than the physical external signal caused, and therefore not as high priority driving in getting satisfied or resolved. Also, since emotional signals are more complex and solutions are more complex requiring more time, their resolution follows the more simple physical induced feelings 311 which must be satisfied first, giving them a higher priority or by analogy with Maslow's need. In like fashion, feelings from thoughts 315 and consciously invoked memories, from cognitive signals, are generally less immediate from a survival or feelings resolution imperative, than those from internal biological/biochemical 313 signals, and therefore generally get satisfied in time after the feelings from emotional responses have been satisfied. Hence a hierarchy of needs whose feelings satisfaction prior in time is drawn pyramid-like in structure in FIG. 3, depicting the demarcation between the different types of induced feelings and their general priority in getting resolved, from those on the base satisfied before those on toward the top cornerstone, called the "self actualizing" by Maslow.

The question of usefulness of this model is already answered by the widespread teachings and use of Maslow's Hierarchy of Needs, where an individual's needs are based on where an individual is in relation to the Maslow Hierarchy of Needs pyramid. In an aspect of the invention, where an individual "is" can be better answered by how that individual feels and the type of feeling that they are experiencing, since feelings will supercede the established "needs" hierarchy because the feeling in the Maslow Hierarchy of Needs are general, and the signals representing the needs in the FIG. 3 feelings hierarchy are specific and time element more closely tied. This embodiment of the invention leads more accurately to what decisions and choices an individual will most likely make in priority, based on the resolution of needs to increase pleasure or decrease pain, in a net resultant sense. Thus electronic applications can be programmed to use emotive intelligence to better predict behavior and offer choices based on resolving feelings in priorities structured in the model of FIG. 3, starting from the bottom physical and moving toward the cornerstone, cognitive. An example of this in consumer behavior is the prediction of an expensive auto purchase. While Maslow's model predicts that an individual who is well off financially with good income and home, family and social associations is a likely candidate to purchase an expensive vehicle, that same individual may have an intense fear from an impending job loss or depression from a bitter divorce, either of which emotive conditions in the FIG. 3 model would dictate behavior of another type, behavior to alleviate the pain from fear or anguish respectively, before indulging in the pleasurable experience an expensive car purchase brings.

In a more complicated experience where there exist multiple feelings simultaneously on a particular subject matter generally represented by text strings, labels or words, a convention setting the pleasure 309 direction towards the pyramid key stone and the pain 307 direction toward the pyramid base direction is followed, the feelings although existing in different zones 311 313 315 will combine to give a general "gut feel" net feeling by combining degrees of pleasure or pain using feeling superposition, the net resultant operating on the text or words. Thus, feelings of all types are treated as signals, neither negative nor positive, signals with a vectored direction into the pleasure or pain space, traveling with associated text or words. This makes calculation of resolution from emotive shifts and emotive displacements possible and eliminates the social and cultural rules which plague other models and preclude any coherent or valid presumptions without value judgments.

FIG. 3 model allows for the combination of related feelings on a particular subject or set of text string(s), word(s) or act(ions) through superposition. The feelings are related to a common subject generally an associated text or words. An example of a superposition treatment of the feelings, emotive_state/intensity_value, could be an individual experiencing physical feelings of hunger/6 and thermal discomfort/2, net 8 in the pain 307 intensity direction, will feel "worse" than an individual feeling hunger/2 and thermal discomfort/1, net 3 in the pain 307 intensity direction. In a more complicated example mixing pleasure and pain states, an individual feeling confident/9 317 at getting fed but hungry/8 319, net 1 321 in the intensity pleasure 309 direction, and therefore still "feels better" than an individual feeling anxious/3 at getting fed but hungry/4, net 7 in the pain 307 intensity direction. Thus the combination of superimposed feelings can provide emotive disposition totals, by algebraic arithmetic. In more sophisticated models, the physical, emotional and cognitive induced feelings can be weighted differently to yield better predictions on overall net feeling dispositions through superposition of diverse feelings, treating each feeling independently and combining those along a common subject matter. As above, the subject matter is carried in the text strings, upon which the combined emotive pain or pleasure operates.

FIGS. 4A through 4D is a exemplar table of an emotive state set with columns for feeling state names 401 in alphabetical order and associated hex code 403 order, State Name 405, Label 407, graphic illustration 409 and pain/pleasure 411 attribute designation for each state.

A Basic Emotive State Set

Although useful for interfaces, the graphics 409 representations are not needed for internal processing. This is shown below in emotive shifts, displacement and finite state machine architecture etc. where the emotive state/intensity and associated text are what are used in processing. Further more, an emotively enhancing interface can use verbal inputs in lieu of or concurrently with face glyph sets. The graphics in FIGS. 4A-4D table are only examples and their generation can be various. The faces glyph graphics 409 in the table are hand drawn manual figures that may fit for some electronic interfaces and not others. This table does not purport to be a complete set or even a good set of such depictions, but it is an implementation of an emotive "alphabet" which is useful for illustrating a first cycle of operation. Thus the Table in FIG. 4 emotive states and their associated attributes will be useful in application interface displays an the emotive intelligence involves the processing of the emotive content when it becomes available to an application as software entities described above.

Mapping Emotive Language and Symbols

Figure 5:
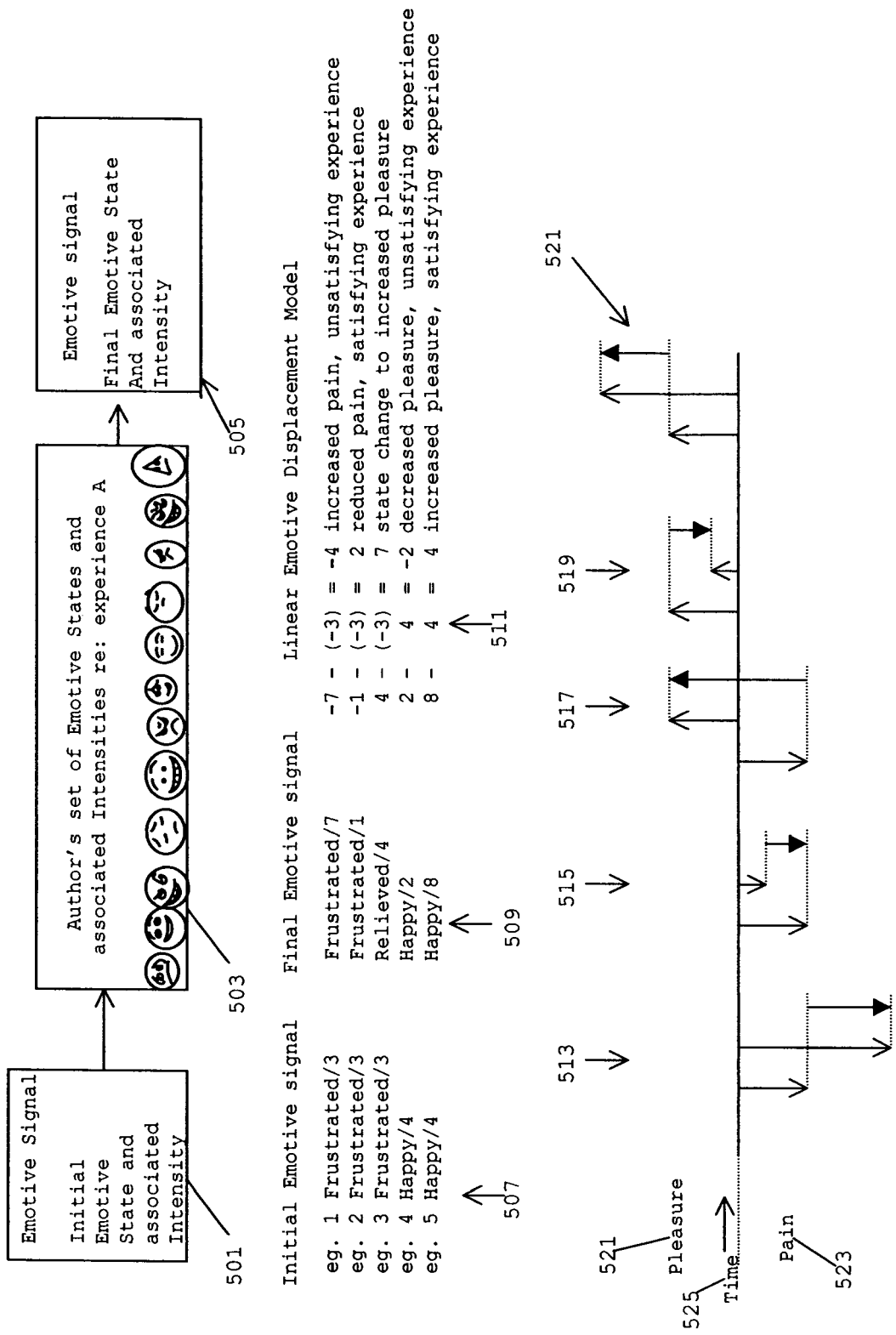
FIG. 5 is an illustration of a net emotional satisfaction metric from an emotive shift calculation in accordance with an embodiment of the invention.

Changes or shifts in emotions are commonplace but currently capturing a feeling is a challenge. In addition, myriad words and large numbers of names represent different feelings making it difficult to track feelings. The result is a general lack of any objective or cohesive models, cultural and religious contradictory teachings, and psychological teachings that do not handle the linguistic realities of emotions. To add insult upon injury, feeling names are separate from the associated text, but can be embedded in the text as text strings or coupled graphic representations. Natural Language Parsers (NLPs) can tokenize the parts of speech and emotive compilers can decouple the feeling text words from the text. Once feelings words or graphics are decoupled from the text, feelings in the form of emovectors, state/intensity pairs, can be processed. FIG. 5 illustrates examples of algebraically combining two emovectors in the pleasure-pain vs. time plane to derive a net satisfaction calculation regarding a subject or action represented by text or words.

Any experience or action will begin with an author's initial emotive state and associated intensity 501. The emotive signal from that initial state 501 can be automatic or introspected, or accesses from the author's experiential database 503. Any new experience will resonate with the author's experiential database 503 much like an incoming signal in an electrical "tank circuit", giving an identifiable frequency which is amplified to the conscious level and changes the initial emotive state. This brings about a resultant temporal state, labeled a final emotive state and associated intensity 505 signal, resulting from the experience. If the final 505 and initial 501 emotive signals are evaluated when the memory of each is discernable and separate, then a numerical calculation corresponding to the emotive shift can be made, providing the net satisfaction or dissatisfaction experienced from the event or circumstance generally represented by the associated subject or action text string or words.

The initial emotive signal 507 for a series of five examples can vary and is succeeded by an appropriate final emotive signal 509, shown for the five examples respectively, which demarks a termination at a particular experience allowing for a calculation 511 to be made, and shown for the five examples respectively. An actual graphical solution space of the emotive vector is the Pleasure 521/Pain 523 vs. Timeline 525 plane. Each emotional state is characterized as being pleasurable or painful, FIGS. 4A-4D. In a simple emovector shift calculation, the resultant satisfaction is the difference of the Final Emovector 509 from the Initial Emovector 507. Because emovectors are a vector quantity, the difference is vectoral and must take into account the direction and magnitude of the final and initial states operating on the associated subject or action. String operations may be such things as string or substring comparisons, concatenations, tokenizations, parsing, translations, and all manner of mappings and manipulations.

In example 1 513, the final state is Frustrated with associated intensity of 7, from an initial state of Frustrated at intensity of 3. The vectoral difference would be a resulting increase in pain intensity of value 4, clearly an unsatisfying experience. Example 2 515 results in a decrease in pain, a satisfying experience. Example 3 517 contains a pain-to-pleasure space change with a clear net satisfaction which includes the complete elimination of painful state to a final pleasurable state, thus compounding the pleasurable final state. Example 4 519 shows a reduction in pleasure from happy with intensity of 4 to happy with intensity of 2, an unsatisfying experience yet in the pleasure space. Example 5 521 is satisfying because the pleasure of the experience is increased.

Useful applications of emotive changes are made in everyday transactions. For example, a sales person taking a customer for a test drive to see "how it feels" or a retailer encouraging a customer to "try on for size" merchandise to actually use an item in an appeal to the buyer. The before and after bounds the experience/subject/action in an emotively measurable way, resulting in a sale or not, depending on the degree of satisfaction/dissatisfaction. Likewise in on-line and computer applications, there is a before and after state, the resultant favorable feeling adding weight towards consummating a deal. In a website application, promoting a service or looking for feedback on its service, a website search engine seeking to adapt its search strategy to a particular user, a complex service with many factors seeking to understand its customers better. All these and many more instances provide discernable emotive shifts to be translated to numeric values and metrics that provide data for processing, understanding and improved products or services. While the physical contact or face-to-face interactions are common and calculated almost at an unconscious level, using the emovectors programming entities, the unconscious becomes numerical data useful for programming and processing to application features and many useful purposes. While there maybe instances where a client or customer may not wish his/her emotions to be used against them in a negotiation, where the net result will bring a better product or service without increase in direct costs to the client or customer, it will be in their net interest to provide this information. The interface may provide several opportunities to solicit emotive input, and mainly for the customers benefit.

In an embodiment of the invention, a translation between an emotive intensity numeric value and a text string state qualifier in words is shown below. In translating from narrative language to numerical value and vice versa, an aspect of the invention maps the emotive intensity numerical value in a given emotive intensity range to text or word(s) corresponding to the value in the range.

| Emotive Intensity Value | Qualifier Translation or Mapping |
|---|---|
| 1 | Hardly |
| 2-3 | Mildly, a little |

| Emotive Intensity Value | Qualifier Translation or Mapping |
| --- | --- |
| 4 | Somewhat |
| 6-7 | Very |
| 8 | Very much |
| 9-10 | Extremely |

Thus the cognitive communication in the form of text or words embedding and being colored by the emotive content, will at times contain the emotive intensity in the form of "qualifying" words giving the emotive state a vectoral dimension magnitude which can be converted from text to numerical value. Thus all of the emotive numerical metrics above also apply to vectoral emotive character extracted from text where the author expresses qualifiers in association with the feeling words or emotive state.

Emotive Displacement

Translating emotive content involves several aspects. One aspect of emotive equivalencing is finding emotive vectors which translate common usage meaning between similar emotive state words by determining the associated emotive intensity range of one emotive state word relative to another. An aspect of the invention for equivalencing involves translating among emotive content to arrive at the author's intended meaning. Stated another way, calculating an emotive displacement from an initial feeling to a final feeling through various intermediate feeling words. This latter aspect also involves a solution to different words used to describe similar emotions.

Figure 6:
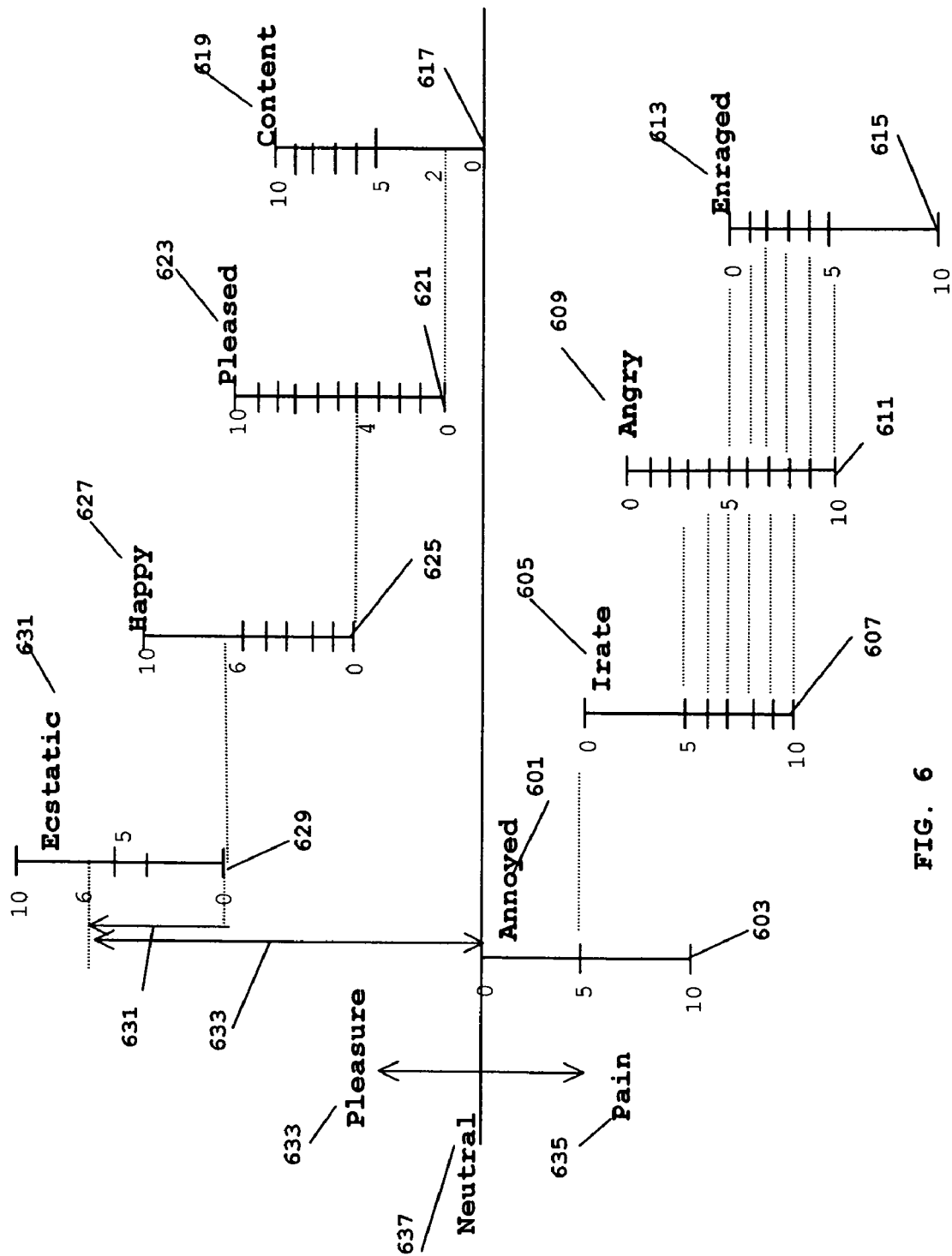
FIG. 6 is an illustration of emotive displacement calculation in accordance with an embodiment of the invention.

FIG. 6 is an illustration of emotive displacement calculation in accordance with an embodiment of the invention.

This is done by using a two dimensional space wherein pleasure and pain are opposing directions on an orthogonal time axis. Emotive displacement from an axis by algebraically combining two or more ranges of similar emotive states shifted relative to each other starting from the emovector state range and contiguously connecting the incremental shifts between the ranges and the point from which the displacement is to be measured, using meaning related emotive states and their associated bounded ranges as scale extensions to determine emotive displacement from an emovector to the origin pain-pleasure orthogonal axis in FIG. 6.

Emotive Equivalence

There are certainly many more words in a language that describe emotive states, than are needed in defining an emotive set of individual character states. For example there are at least 8 words in the English language Thesaurus that represent the similar meaning for the emotive state word enraged. The FIGS. 4A and 4D emotive state set is therefore expandable to meet demands of a robust language with emotive state synonyms. Likewise, a subset of the Table in FIG. 4A-4D can be found to meet the required base set of emotions from which all other language symbols can be linked in vectoral fashion, revealing that the Table 1 somewhat arbitrary. Moreover, an aspect of the invention is to accommodate common usage of words representing similar emotive states that are not in a face glyph alphabet set of possible choices. Emotive words defined in a thesaurus or dictionary is meaning related and provide a start in equivalencing among emotive vectors along similar emotive space directions.

An objective and consistent difference between feeling words related in meaning to other feeling words under a thesaurus or dictionary definition can be used to interpolate similar feeling words and also to other and non-related feeling words and symbols occurring across from or reflecting off the Pleasure/Pain 635 Neutral 637 axis. Thus emotive state words with synonymous emotive state words can serve as an emotive state set expander to a much larger working emotive state set. In implementation, the associated intensities of the different emotive state words must scale the intensity of those words to common usage to maintain an equivalent emotive vector, i.e. similar emotive state words which differ by emotive intensity value only must be translated by shifting the emotive intensity ranges relative to each other to be reasonably near common usage of those emotive state words in a particular culture or setting. Thus the thesaurus or dictionary meaning of a subject feeling word is generally within that range of meaning, differing usually in intensity only.

Emotive vectors represent an emotive state accompanied with an author normalized emotive magnitude or intensity. In an embodiment of the invention, a numerical value for emotive intensity will range from 1 to 10 with 1 being the lowest intensity felt in a particular emotive state by the author and 10 being the highest emotive state intensity felt by the author. Emotive vector displacement translations can be accomplished to extend the emotive state word number to apply to most feeling words. For example the emotive vector, emotive state/intensity pair, of (IRATE, 10) 605 would be emotively equivalent to the emotive vectors of (ANGRY, 8) 609 or (ENRAGED, 3) 613. (ANNOYED, 10) 601 is equivalent to (IRATE, 5) 605 and so forth. These are all associated with set ranges of 0 to 10 603 607 611 615 and ranges 617 621 625 629 for the emotive states Content 619 Pleased 623 Happy 627 and Ecstatic 631 respectively and related in meaning, falling in the pleasure space. The relative placements of the emotive state ranges are the bridge that allows the total emotive displacement calculation. They can be collectively determined by linguists or set in some other fashion, but they become the translation bridge between and among feeling words.

The emotive intensity range shift magnitude is determined by common usage of the emotive state word. Emotive equivalencing between emotive vectors, emotive state-intensity pairs, translates between words that have similar emotive states but vary by emotive intensity range placement in the pleasure/pain space. A set of emotive intensity range scale translations for similar emotive state words can be defined and stored for use and for the purposes of translations between emotive state-intensity pairs. FIG. 6 graphically illustrates the translation of emotive states though the process of emotive equivalencing and total emotive displacement from Ecstatic 631 to Enraged 613. Under the emotive state word ANGRY appearing in a thesaurus, one would find annoyed, irritated, fuming, mad, livid, irate, heated, cross, incensed, enraged, outraged and infuriated. One can translate between those thesaurus-defined emotive states by positioning the associated intensity range up or down in range scale to align with common usage of the terms to describe reasonably similar feelings, first relative to themselves and then relative to the neutral 637 axis. In FIG. 6, we graphically defined the incremental emotive displacement by range shifting from Annoyed to Irate as 5, Irate to Angry as 3, and from Angry to Enraged 5. This can be done by committee of qualified experts and shown here for illustration of a first order cycle of operation. The total displacement from the neutral axis 637 to the highest Enraged intensity is determined by adding the incremental feeling word displacements between the desired unknown and the intermediate incremental displacements, here Annoyed at 5, Irate at 2, Angry at 5 and Enraged at 10, yielding a total displacement on the pain space of 22. While the relative emotive displacement between states can be determined by language experts and thus more objective, the actual emotive intensity of the user chosen state name and intensity is chosen by and normalized to the author, and thus totally subjective to the author/sender. By translating emotive states through emotive equivalencing to determine total emotive displacement, a relatively small face glyph set or emotive table set can be made to represent a much larger vocabulary of feeling words. Given an emovector 631 Ecstatic/6, the emotive displacement is calculated by the algebraic sum of the intermediate ranges of related meaning states Happy 627, Pleased 623, and Content 619 with incremental range displacements of 6, 4 and 2 respectively. Thus the total emotive displacement from the neutral axis of the emovector 631 is the sum 6+6+4+2 totaling 18. Thus and embodiment of the invention uses meaning related emotive state ranges as scale extensions constructed contiguously or overlapping to a neutral pain-pleasure axis, in determining total emotive displacement from an emovector to the origin pain-pleasure axis.

Internet Business Models

Vendors are trained experts in targeting their markets, and can determine the mind set and state of their most likely customers/clients. This may be a product/service dependent on a function of the client/customers emotive disposition when reaching the website. Vendors who know their target customers know what customer disposition/intent/desire/needs are well satisfied or satisfied best. Thus a vendor can chose what initial emotive disposition(s) could be their best client/customer. A vendor then associating their product/service for particular emotive state/intensity can thus more efficiently handle the clients/customers that they are most likely to satisfy and therefore keep as repeat customers. A true relationship can be cultivated between producers and consumers, because although business based, there is the emotive component which is satisfied or not, depending on the delivery/performance between parties. This performance is best when clients/customers are best satisfied. An aspect of the invention is to most efficiently identify products/services consumers require and most efficiently identify consumers that vendors are most likely to service with the highest satisfaction.

Thresholds and Customer Profiles

Emotions act as precursors to searches for alternatives or options to resolve the feelings. Furthermore, a given emotive intensity reaching a set threshold will trigger actions or behavior by the author. Individuals all have unique thresholds for degrees of pain that they will tolerate or degrees of pleasure which will spur action or addiction. Emotive thresholds are therefore emotive intensity values which when attained by an author, have a certain probability of triggering some action or response by the author.

Of course individuals are all unique, therefore distributions and statistical means can be applied to predict actions with a known degree of precision or at least heavily weigh the desired or expected action or behavior for deriving thresholds. Where a customer is "not motivated", emotively ambivalent, or with low emotive threshold, sales devices or additional degrees of persuasion must be used to consummate a transaction, to move the customer to make a decision. "Motivated" consumers are more likely to complete a transaction over less motivated consumers, and with less compelling persuasion or effort, because those consumers are emotionally nearer their threshold limit for action on a particular subject matter. In certain instances, thresholds could include multiple feelings. Feelings of physical discomfort may not prompt an action, but feelings of physical discomfort in conjunction with a small fear intensity may trigger an action to move to a better location, where as feelings of physical comfort in conjunction with a small fear may not trigger the action or may trigger another action.

Markets look for a motivated buyers and reliable sellers. Providers who understand their product/service also know the emotive profile of its market segment, as well as the emotional content of a consumer most likely to complete a transaction. The providers' ads or market strategies will often target those consumers that feel a certain way. Thus, providers can construct emotive profiles, meaning emotive states with accompanying intensity thresholds, which describe their most likely customer emotive dispositions. A Wills & Trusts attorney may have a profile as simple as clients who are worried at a threshold above 7, regarding the subject of death or death of a loved one." A car dealer may find "anyone experiencing pleasurable emotions with intensities above 5" a more likely customer. Emotive profiles are provider's customer emotional criteria or filters in the form of list of one or more emotive states and associated thresholds, and or combinations of such. A vendor selling pizza will look for customers who are feeling from hungry to very hungry. A customer in a painful emotion may wish for a product/service that will transfer them to a somewhat less painful condition; a customer in a pleasurable emotive condition may want something that will include others in an activity, sharing the good mood. The scenarios are vast but the commonality is that feelings are used in anticipating and satisfying needs, hence a network can quickly narrow the search and satisfaction of these needs, members responding with offers to potential customers most likely to consummate transactions, those customers being of a particular emotional persuasion.

From a standpoint of search efficiency, a small effort by consumer through introspection can initiate and drive a possible universe search from without electronically. Emotive content, relatively easily obtained by consumers with needs through introspection, can propagate into a search space universe self configured for a "motivated" customer based on the universes knowledge of its customer emotive disposition. Furthermore, providers can customize their offerings likely to satisfy the customer, because they are dealing with a likely customer's motivation or need. Moreover, customer interest is directed to most likely targets, eliminating the indiscriminate and wasteful Spam method, while efficiently meeting the advertising needs of businesses.

Figure 7:
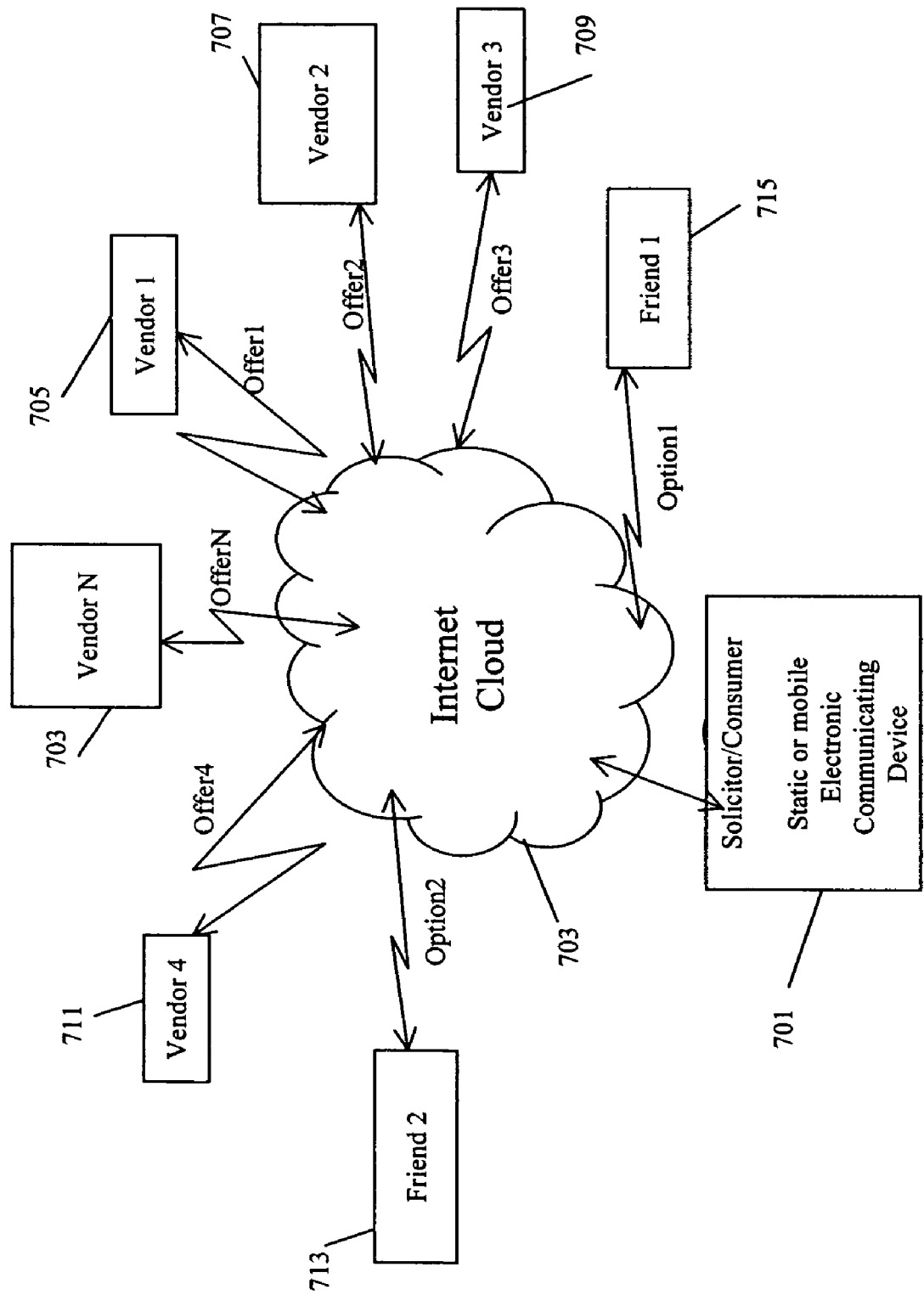
FIG. 7 is an illustration of an eCommerce topology carrying an emotive intelligent Internet business model in accordance with an embodiment of the invention.

FIG. 7 is an illustration of an eCommerce topology depicting an emotively intelligent Internet business model.

In its simplest mode, a consumer 701, static or mobile, broadcasts his/her emotive content, into the network cloud 703. Thus providers of goods and services 703 705 707 709 711 preferring a customer with specific emotive state(s) and associated set emotive intensity threshold(s) and regarding a given subject matter, a customer emotive profile, respond with offers either in real-time or at a later time, depending on the emotive content urgency, and depending on the customer's emotive state, intensity and other strategic factors the provider may have. An embodiment of the invention model is not limited to providers, as friends can also respond with options where emotive content triggers a friend's emotive profile for response, depending on the emotive desire eliciting satisfaction sought and in the temporal constraints requiring its fulfillment or resolution. The emotive intensity, urgency, and the geographic distance of the consumer 701 from the vendor/friend determine how quickly the interaction can and should occur for the customer/friend's 701 emotional resolution and hence most like acceptance of performance consummation.

E-commerce Real-time Client Satisfaction

An aspect of the invention is that all emotions and feelings are good and positive, even "down" or "negative" emotions are good positive signals. Thus no value judgments are made. Since emotions are signals of degrees of pleasure or relative pain, an increase in pleasure or a decrease in pain are indicators of increased satisfaction. Alternatively, emotive decreases in pleasure or increases in pain indicate dissatisfaction. Thus emotive measurement is followed by a calculation using emovectors, the emotive state indicating the direction of pleasure or pain, and the emotive intensity is the magnitude or strength of the pleasure or pain attribute. In an invention embodiment, the author, also sender, seeker, consumer, user, etc. may enter his/her emovector before experiencing the provider good/service, then experiences the good/service and enter their emovector again. The emotive shift or change provides a net satisfaction by taking the emotive vectoral difference. In the event of a client who is predisposed to or momentarily in a particular painful emotive state, an embodiment of the invention can still measure the degree of satisfaction or dissatisfaction from a standpoint of reduction or increase in pain. A website provider may alter its price on certain items based on customer emotive content, or offer other products, services or features based on the customers given emotive state and intensity as the intensity nears set emotive profile thresholds. A customer scoring higher on the income demographic with emotive vector of annoyed/8 may not be as persuaded by a price discount as they would an alternative model recommendation with specific features. A customer scoring lower on the income demographic with emotive vector worried/5 maybe more amenable to a price discount, than certain other model/service features. Thus the initial emotive content can drive the sale pitch direction, customizing the pitch to specific customer needs and motivations.

Emotional shifts or changes occurring during any e-commerce transaction reveal consumer satisfaction or dissatisfaction with the process or service. Unsatisfactory process will indicate perhaps a better webpage implementation; unsatisfactory service will indicate that a change in processing customer input is required. Therefore, an emotive vector elicited before and after product/service can be used to calculate the emotive shift or displacement to provide a measurable quantity regardless of the consumers starting or leaving emotive state. The question arises then, how to measure or calculate customer satisfaction. Emotive state is not sufficient, because how a customer or client initially feels is a result produced from a past circumstance. While this state is important in what product/service that client or customer would need to satisfy a need or desire, it does not help to determine whether that product/service fulfilled that need or whether that customer's motivation was serious toward a purchase. Moreover, satisfying emotive position changes or shifts after product/service, generally the associated subject or action associated with the feelings, is delivered. Satisfied consumers are necessary to build website repeat business, site loyalty, brand loyalty and continued business. Everybody likes and strives for a "happy customer", or one that walks away happy. Emotional changes are the fundamental gauge in defining client satisfaction. Examples are users of search engines; user emotive content before and after a search will indicate whether the search was helpful and determine whether that searcher will return to the website.

Subsequent searches can be based on previous user emotive inputs, allowing the search engine to adaptively or programmably alter its search algorithm, using the searchers emotive attributes or the degree of satisfaction or dissatisfaction. For example, a user searching on "automobile" entering emotive vector of happy/9 may be seriously looking to purchase while a user searching on "automobile" entering an emotive vector of concentrating/3 or annoyed/5 may be researching the automobile industry, and the search algorithm may weigh the ".org" more heavily than ".com" sites. However, if the concentrating/3 or annoyed/5 author emovectors change to concentrating/6 or annoyed/8 respectively, and the search results return many hits, then the search is not producing the type of results needed with high enough priorities. Changes in the search algorithm weightings or additional search terms may increase satisfaction. However, if the number of hits is small or medium, the dissatisfaction may be better remedied with a higher consideration of the vendor emotive profile preferences.

Figure 8:
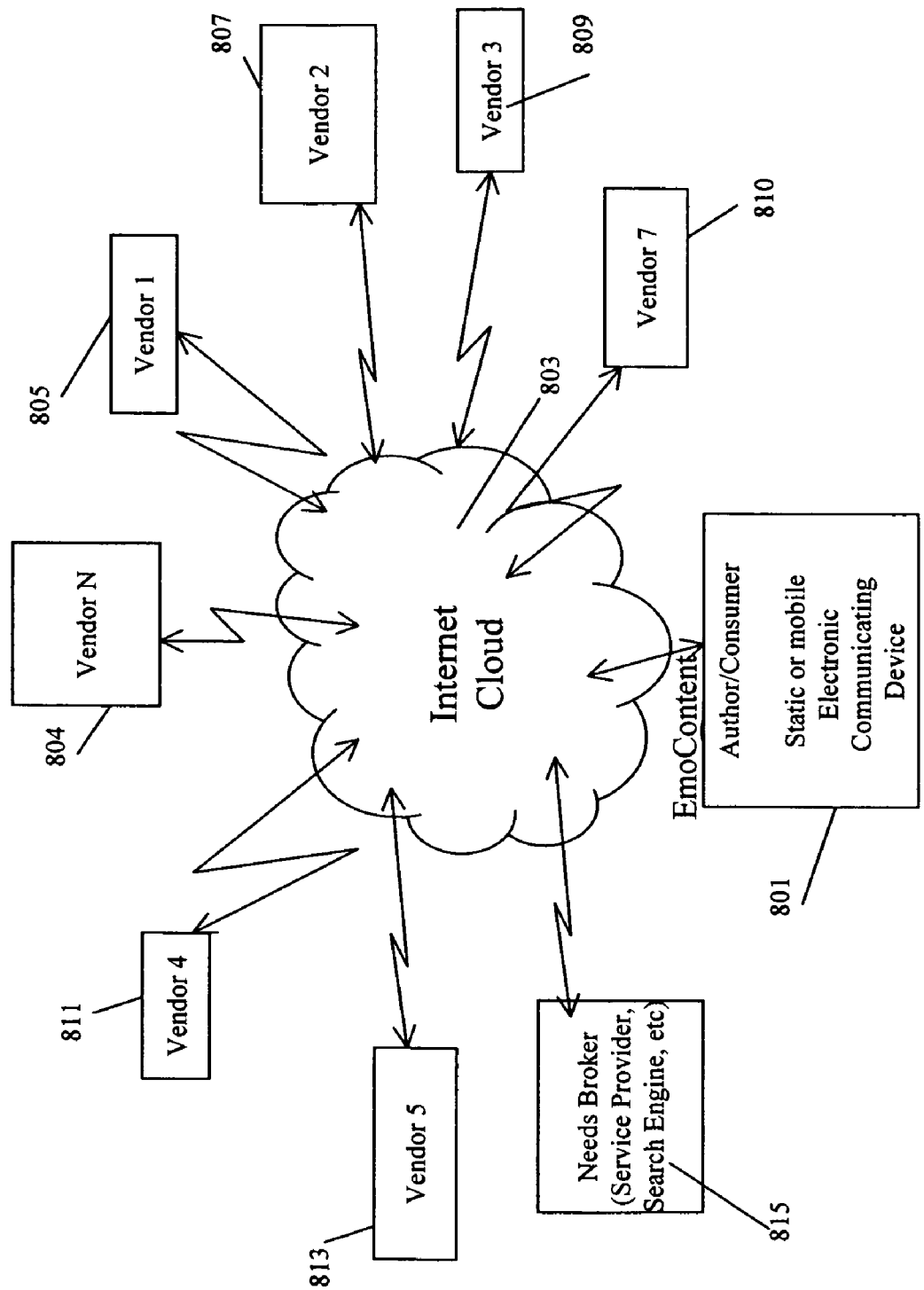
FIG. 8 is an illustration of an eCommerce topology carrying yet another emotive intelligent Internet business model in accordance with an embodiment of the invention.

FIG. 8 is an illustration of an eCommerce topology carrying yet another emotive intelligent business model in accordance with an embodiment of the invention.

Although the simplest way of requesting service, broadcasting one's emotive content onto the network may not be the most efficient implementation in a business model. FIG. 8 illustrates an emotive intelligence Internet business model that applies an emotive content Broker 815. A consumer 801 makes his/her needs known to the emotive content Broker 815 via the transmission of emotive content and identification. This can be done through any network or Internet 803 accessing device. The need(s) transmission represents a request for offers, to satisfy the emotive content. The Needs Broker 815 can be as little as a web service with a database, knowledgeable of provider addresses and their emotive thresholds. The broker 815 intermediates the emotive content resolution for consumers, connecting consumers with providers servicing the particular emotive content of consumers 801. The Needs Broker 815 can also be something more generic like a search engine web service, since search engine websites have already stored vast quantities of webpages, provider addresses, and 1) can quickly identify vendor candidates by ascertaining geographic proximity of service/product source to consumer, 2) can identify the temporal constraints of consumer, from emotive urgency, and response time required for vendor to reach consumer, and 3) have the emotive profiles serviced by vendor or vendor target markets based on preferred consumer emotive disposition. Upon receiving the consumer 801 emotive content, the broker 815 filters for candidate vendors 804 805 807 809 810 811 812, selecting vendors requesting consumers of that particular emotive content or derivative thereof, one such as through emotive equivalencing. The broker 815 then sends the list of candidate vendors 804 805 807 809 810 811 812 with their offers to consumer 801 or alternatively, the Needs Broker 815 can negotiate a model by which the candidate vendors 804 805 807 809 810 811 812 contact the consumer 801 directly, through a channel that is requested by consumer 801. Channels may be email, Instant Messenger, phone, browser, etc.

Emotive Dimension in Electronic Search Space

A challenging issue pertaining to search engines is how to specifically seek out those target vendors without incurring excessive hits. The utility of the searchers emotive state/intensity and associated text allow search engines more dimensions on which to filter out unwanted hits and also adaptively construct hit prioritizing algorithms, so that consumers' individual customized needs are served, through application of their emotive content in string operations. String operations includes all that is currently done in providing service, such as comparing strings, concatenating, finding and using substrings, regular expression operations, text processing, etc.

The market looks for a "motivated" buyer or seller. A motivated consumer translates to more likelihood of consummating transactions and that translates to intense desire to transact business, not disinterested curiosity "Looky-Lous". Thus the provider's emotive content profile will reflect that. The great distinguisher or filter is emotive state and associated emotive intensity. The higher a person's emotive intensity in any emotive state, for example in a range of 1-10 EI=>5, whether the emotive state be anger, fear, sadness, excitement, anxiety, etc, the more likely it is that they are seriously looking for a product or service and the higher the likelihood that the individual is going to take some action to achieve satisfaction. The less intense the emotion, for example if the action threshold is 5, EI<5, the more likely the consumer is simply researching something out of curiosity without intent to take an action.

In addressing search algorithms, search engines may weigh commercial sites, public domain sites, news sites etc, differently as functions of emotive content. For example, EI=>5, commercial sites like .com may be weighed higher than .org sites. When EI<5, search is research based and .org sites weighed more heavily.

Furthermore, long candidate hit lists from searches can be reduced by feedback emotive content from consumer 801, in a feedback loop to broker associating emotive content with a previous transmission, i.e. progressive searches starting with or leading to frustration or increase in frustration intensity type emotive contents indicate that the candidate hit list is ineffective or leading to counter-productive results. A consumer-customized search algorithm restructuring can then be adaptive, conforming with better hits more closely aligned with changes in emotive content received, since emotive content is well defined, distinguishable and have known characteristic behavioral needs and requirements.

Automated Intelligence

Some applications require that the "machine" make more and better decisions. Telling "it" what to do becomes burdensome, not fun for the player or operator. Electronic games are an application where the character manipulation becomes tiresome, and the players eventually claim that the game "lacks intelligence." Frustration increases because the game characters cannot do even basic things expected. The reason being that it is so extremely difficult from a programming standpoint to anticipate and program for every conceivable circumstance that can reasonably or predictably occur in the game. "Machine Intelligence" outside of very limited applications like Chess, having large programming and commercial resources available, has been an industry joke.

Figure 9:
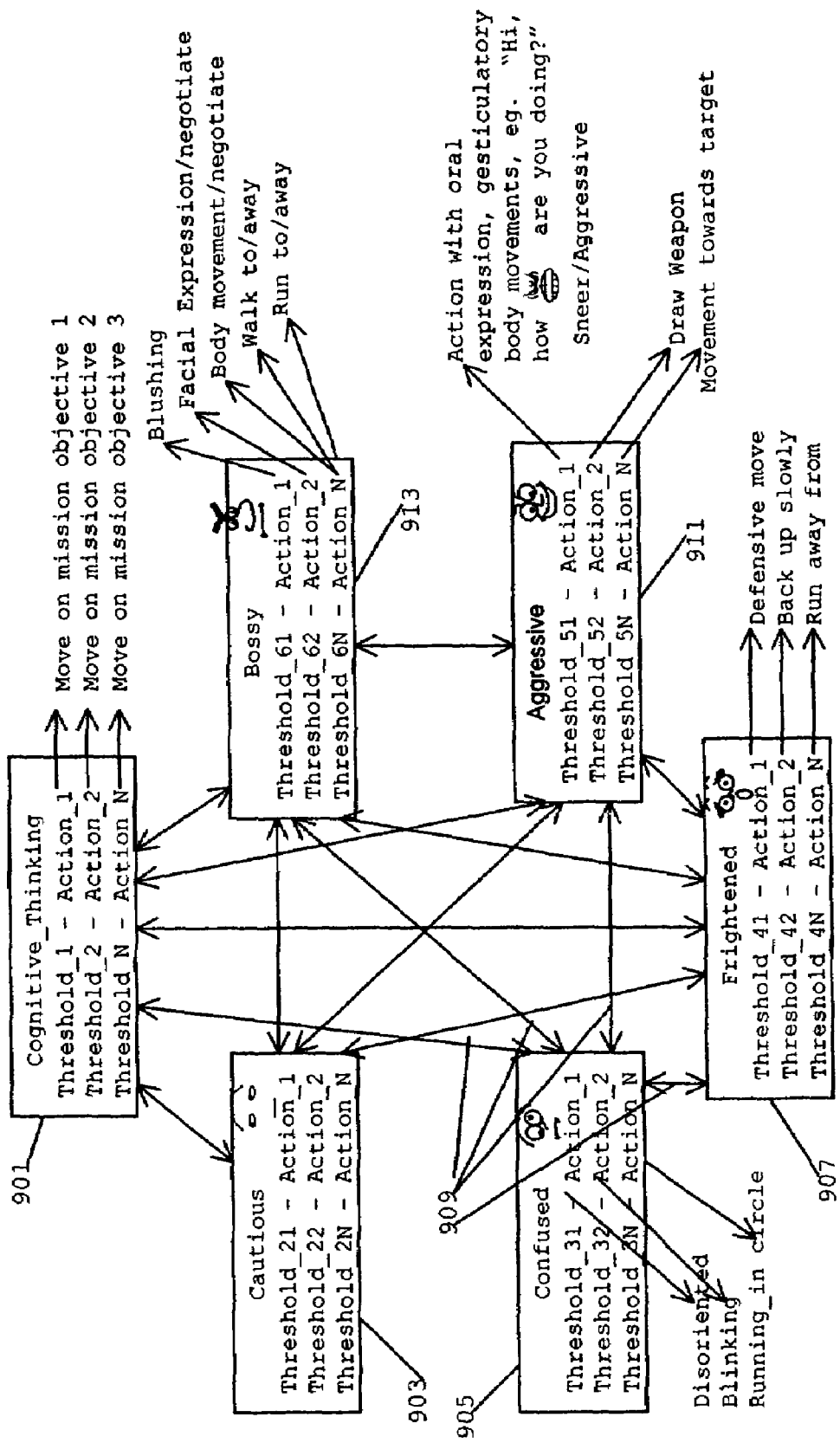
FIG. 9 is a high-level block diagram of an emotive object finite state machine in accordance with an embodiment of the invention.

FIG. 9 is a high-level block diagram of an emotive object finite state machine in accordance with an embodiment of the invention. This finite state machine is architecture for an autonomously responding character, reacting much like an emotionally intelligent entity or sentient being. FIG. 9 represents the emotional makeup or emotive inventory of a creature in an electronic application, here composed of Cognitive Thinking 901, Cautious 903, Confused 905, Frightened 907, Aggressive 911, and Bossy 913 emotions. These emotion constructs have thresholds corresponding to the creature's emotive intensity in a corresponding emotive state. External stimuli act to shift emotive states of this creature, actions/behavior Stimulates causal response with Interacting characters or players.

Emotive states can undergo shifts 909 to and from other emotive states based on external stimuli received through actions of other game characters or programming directives. Each emotive state has one or more threshold actions based on its emotive intensity achieving a set threshold value, allowing the creature/character to respond to different stimuli of variable degrees and responses. Also, the threshold values themselves can be programmed to change based on leaning, or stored event-behavior-response data. If the Aggressive 911 state is triggered from an external stimulus, the emotive intensity associated with the state will trigger a threshold action of oral/gesticulatory behavior, drawing of weapon, or moving threateningly toward the target.

Simultaneously, the character and character actions would be displaying emotive expressions corresponding to emotive states with associated emotive intensities, morphing character display expressions with corresponding character emotive state and associated intensity changes. This can further be synchronized with prosodically outputting character text and visual display corresponding to associated emotive state and associated intensity. The result would provide a fully intelligent multi-dimensional character that can autonomously function in responding action, outwardly display emotional changes morphed in direct correlation to the emotive shifts and emotively justifiable prosodically enabled verbal output.

Events could provide stimuli also for Cognitive Thinking by way of mission objective; for example an external event such as target retreating, hostile action by target, etc. could trigger actions to attain mission goals not emotively triggered.

Many of the most popular electronic games have characters center stage. As illustrated in FIG. 9, characters can be programmably represented through their emotive states in a finite state machine architecture, whereby the emotive shifts in the character emotive inventory dictate behavior programmed as function of emotive state/intensity, changing the state in the finite state machine architecture. Emotive intensity can also be a function of time dissipation and space proximity to perceived threats, actions by characters, players or environment. Thus interacting characters change proximity relative to each other, which trigger emotive states/intensities responses of characters, which in turn react or behave, based on thresholds of emotive intensities achieved. The programming architecture becomes simple while accommodating vastly complex, even intelligent response behavior, programmably. The associated graphics become simplified as the creature's facial expressions morph corresponding to emotive shifts and emotive displacements, corresponding a creatures emotive makeup to situational circumstance and actions of other characters, in turn producing emotive shifts and response actions. Emotive morphing adds a real world feature that aids players in identifying visually, from creature facial expression morphs or actions made, what strategy a character is attempting and to adjust player response accordingly.

For example, a greedy overlord can be shot and killed, if the player can overcome all his minions by sheer firepower, or the overlord's greed can become a player's ally in getting around the overlord. Alternatively, a player building a city may have to deal with the emotions of city council approval committee, adverse neighbors, etc. Events can crescendo or escalate in accordance with emotional justification, acts followed by feelings cause and affect. The players have options on how to deal with adversaries, either from the direction of the adversary's emotions or from their own characters. Alternatively, empathy can be heroes, because they know the feelings going on with the adversary, they know the adversary's fears, moods, and tendencies and can predict actions. An adversary may not fear bullets, because they have an armored vest, but they may have an irrational fear of snakes (put in your greatest fear here). The hero then knows when to strike, how to strike most effectively and how to prevail without the use of violence. Even a negotiation may require exchange of emotions and interests assessment based on things other than kill-or-be-killed.

With emotive objects, the elicitation of emotive content can be structured around characters or events in the game to more realistically lead to combat or cessation of combat, which can also be a desired result in traversing a space or circumstance. In addition, characters can have emotional makeup to justify their actions, and this emotional component can be dealt with in the game scenario to direct the action of achieving the game objective through alternate means i.e. without a firefight, killing or senseless slaughter, but by a satisfaction of emotions through negotiation. Negotiation actions are triggered by non-threatening acts or events, which in turn trigger interacting characters and players to perform non-threatening or even friendly acts, which may alter the game path toward more peaceful intents, yet still retain the game-rewarding objectives.

This can be done either internally, with emotive objects, emotive response operations and programming. Initial conditions and options can be elicited from the players themselves in assignment or selection of options or from a stored scenario. Databases of emotions can be set up, stored with text and used with a prosodic interface for voice and also to drive the video character facial properties to correspond with the emotion embedded in the text stream. Synchronicity is preserved through the emotive-text data stream, so that audio and visual emotive responses are driven from the same data stream. Hence, the finite state machine emotive inventory model is a compact and concise way to organize and program application characters giving them intelligence, endowing them with programmable autonomous reactions and providing the corresponding display rendering and verbal prosodic output that is carried by the text output stream.

Other Embodiments of the Invention

While the invention has been described with reference to a preferred embodiment in which the emotive content is transmitted via formats and protocols in UNICODE, XML, HTML data-streams, the invention may be carried out in a different manner using formats and protocols other than those, such as in SOAP, XLS, SGML, ASCII. In fact, the invention is not confined to any particular format or protocol type by may be carried out using any suitable transmission scheme or model. The programming architecture described at a high level can be implemented in most computer languages. The emotive displacement calculations shown were based on a basic one-dimensional vector algebra operation and need not be limited to such a simple model. Emotive vector models can vary in more dimensions and carry more attributes, as any vector can take on more dimensional components and their calculation of displacement will vary accordingly. Emotive Inventories can be extremely complex and include cognitive structures as well as behavioral entities that feed back onto themselves as well. Quirky behavior and all manner of deviation in emotive inventories can be programmable, as we have presented a branch of Artificial Intelligence which has not been studied or applied in this fashion, but is not limited to a cycle of operation show here.

While the invention has been described in detail with reference to preferred embodiments, it is understood that variations and modifications thereof may be made without departing from the true spirit and scope of the invention.

What is claimed is:

1. A method of processing emotive intelligence in electronic devices, the steps comprising:
   obtaining at least one emovector from a communication stream, emovector comprising an emotive state from a set of emotive states, and an associated emotive intensity from a range of intensity normalized to the emovector's author;
   assigning a pain-pleasure attribute and a pain-pleasure scale_value to the emotive state;
   numerically combining the emotive intensity with the emotive state pain-pleasure attribute and value on a pain-pleasure scale from device storage medium for a total magnitude;
   algebraically combining the pain-pleasure scale emovector magnitude with a second emovector's pain-pleasure scaled magnitude;
   obtaining a emovector algebraic result accounting for their pleasure pain attribute direction representing the net emotive shift;
   coupling the emotive shift to the text meaning or text string operation;
   whereby emovector emotive shift provides quantified emotive changes with accompanying text.

2. A method of processing emotive intelligence in electronic applications as in claim 1 further comprising the steps of mapping the emotive vectors to an n-dimensional space with pain-pleasure and time dimensions wherein numerical operations on the emovector's yield resultant pleasure-pain displacement values as a function of time.

3. A method of processing emotive intelligence in electronic applications as in claim 1 further comprising the steps of algebraically combining a first and a second emovector each having normalized emotive intensities aligned in their corresponding pain or pleasure attribute directions, wherein pleasure and pain axis are aligned in opposing directions orthogonal to a time axis.

4. A method of processing emotive intelligence in electronic applications as in claim 3 further comprising the steps of summing uncommon ranges of meaning related emotive state associated range scale extensions constructed contiguously or overlapping and orthogonal to a neutral pain-pleasure axis, summing from the base range of the emovector to the neutral pain-pleasure axis, in determining total emotive displacement from an emovector to the origin pain-pleasure axis.

* * * * *